United States Patent
Clendennen et al.

(10) Patent No.: US 6,642,438 B1
(45) Date of Patent: Nov. 4, 2003

(54) MELON PROMOTERS FOR EXPRESSION OF TRANSGENES IN PLANTS

(75) Inventors: Stephanie K. Clendennen, Portland, OR (US); Jill A. Kellogg, Portland, OR (US); Chau B. Phan, Portland, OR (US); Helena V. Mathews, Portland, OR (US); Nancy M. Webb, Portland, OR (US)

(73) Assignee: Exelixis Plant Sciences, Inc., Portland, OR (US)

( * ) Notice: Subject to any disclaimer, the term of this patent is extended or adjusted under 35 U.S.C. 154(b) by 0 days.

(21) Appl. No.: 09/527,972

(22) Filed: Mar. 17, 2000

Related U.S. Application Data
(60) Provisional application No. 60/125,310, filed on Mar. 19, 1999.

(51) Int. Cl.$^7$ .................. C12N 15/09; C12N 15/29; C12N 15/82; A01H 5/00
(52) U.S. Cl. .................. 800/287; 800/278; 800/298; 800/309; 435/419; 435/468; 435/320.1; 536/23.6; 536/24.1
(58) Field of Search ............... 800/278, 298, 800/309, 287; 536/23.6, 24.1; 435/419, 468, 320.1

(56) References Cited

U.S. PATENT DOCUMENTS
5,886,164 A  3/1999  Bird et al. .................. 536/23.2

FOREIGN PATENT DOCUMENTS
| WO | WO 97/37023 | * | 9/1997 |
| WO | WO 97/38106 | | 10/1997 |

OTHER PUBLICATIONS

Montgomery et al., "Identification of an ethylene–responsive region in the promoter of a fruit repening gene", Proc. Natl. Acad. Sci. USA, vol. 90, pp. 5939–5943, Jul. 1993.
Clendennen, S.K. et al., "Differential gene expression in ripening banana fruit" Plant Physiol., (1997) 115: 463–469.
Bouquin, T., et al., "Wound and ethylene induction of the ACC oxidase melon gene CM–ACO1 occurs via two direct and independent transduction pathways" *Plant Molecular Biology* 35:1029–1035 (1997).
Dominguez–Puigjaner, E., et al., "A cDNA Clone Highly Expressed in Ripe Banana Fruit Shows Homology to Pectate Lyases" *Plant Physiol.* 114:1071–1076 (1997).
Genbank Accession No. X92943 M. acuminata mRNA for pectate lyase.
Genbank Accession No. X95551 C. melo ACC oxidase gene (clone CM–ACO1).
Genbank Accession No. Z93106 M. acuminata mRNA; clone pBAN UU84.
Lasserre, E., et al., "Structure and expression of three genes encoding ACC oxidase homologs from melon (*Cucumis melo* L.)" *Mol Gen Genet* 251:81–90 (1996).
Lasserre, E., et al., "Differential activation of two ACC oxidase gene promoters from melon during plant development and in response to pathogen attack" *Mol Gen Genet* 256:211–222 (1997).
Medina–Escobar, N., et al., "Cloning, molecular characterization and expression pattern of a strawberry ripening–specific cDNA with sequence Homology to pectate lyase from higher plants" *Plant Molecular Biology* 34:867–877 (1997).
Medina–Suárez, R., et al., "Gene Expression in the Pulp of Ripening Bananas" *Plant Physiol.* 115:453–461 (1997).
Lopez–Gomez, R., et al., "Ethylene biosynthesis in banana fruit: isolation of a genomic clone to ACC oxidase and expression studies" *Plant Science* 123:123–131 (1997).
Huang, P.–L., et al., "Characterization and expression analysis of a banana gene encoding 1–aminocyclopropane–1–carboxylate oxidase" *Biochemistry and Molecular Biology International* 41(5):941–950 (1997).

* cited by examiner

*Primary Examiner*—Phuong T. Bui
*Assistant Examiner*—Medina A. Ibrahim
(74) *Attorney, Agent, or Firm*—Jan P. Brunelle

(57) ABSTRACT

The present invention is directed to a melon actin promoter capable of providing expression of heterologous genes, and nucleic acid constructs, vectors, transformation methods, transgenic plant cells, and transgenic plants comprising said promoter.

13 Claims, 18 Drawing Sheets

```
  10         20         30         40         50         60         70         80         90        100
gctattaaggcttgatcccaagaccctcgctctctatcttcgcaacaactcacgtcattgttattggttccttttgccttcgtctcaaatgtctcata
cgataattccgactaggttctgggagcgagagatagaacgcgttgtgagtgcagtaacaataaccaaggagaaaacgaagcagagttacagagtat 110        120        130        140        150        160        170        180        190        200
ttgtataatcttcaagaagggtattcacgacctcctacgatgaaggagtgcaccctcgtcgttctgttccttcttatcattgcttcgttaggaaacataa
aacatattagaagttcttcccataagtgctgaggatgctactctcctcacgtgggagcagacgagcaaagaatagtaacgaagcaatccctttgtatt 210        220        230        240        250        260        270        280        290        300
taactcgggaaggagacacaaacaatgtttatagtgatgagtcatgtaaggaaggagagaagaaagttgtcgtgatgcctcttcccttaaccttt
attgagccttcctctgtttgttacaaatatcactactcagtacattccttcctcttcttcaacacagcactaacgaggaagggaattgaaa 310        320        330        340        350        360        370        380        390        400
gttggatgaaaagatcattaggactcgaaattttaaaagtgagaaggagaccaagatacctcctcatagcaagataagataccgagatgaat
caacctacttcttctagtaatcctgagctttgctacattcaataattctttcaaaattttccacctcttcctctgggagtatcgttcattcctataggctctacta 410        420        430        440        450        460        470        480        490        500
gtgaggaagaaaacgatagcaaacgatgtaagttatcatgaaaatatgagaaccctcatgatgagctttagtgtcactcgataattaa
cactcctcttttgctatcgtttgctacattcaatagtacttcttttatactcttggagtactactccgaaatcacagtggagcttattaatt 510        520        530        540        550        560        570        580        590        600
agacgaggataacacgtgcaacaacaaggacataaacgataaaggcgttgattgacgagacgcttgatgagaccaaagtcgaacataatacatattttttaa
tctgctcctattgttgcactgttgttattcctgtatttgagacagggacaaggcagctcctgctgaagtcgacacgttgattgccgaatactgaacaagttcagcttg 610        620        630        640        650        660        670        680        690        700
gataaaaaaaaagtaaagaagtgtatttagaagaaaaagaaatataattttttgagaatttgtccgaatacgaataatacatatatttgaa
ctatttttttttcattcttctactataaatcttctttttctaatattctaaaacatcttaaacaggcttatgcttatatatattaataaaactt <TRX14_B
                                         750|
 710        720        730        740        760        770        780        790        800
tattaataaataagataccaacgcgtcgcttggttcatcgtctttcttaacgcggcggaacgtgaggccgacaaaggttcatgattccta
ataattaattattctatgttgcgcagcgaaccaagtagcagagaaagaaattgccgcctgcactccggctgttccaagtactaaggat
```

Fig. 1A

```
<TRX14_A                                                                                              >putative_TATA
    |       |       |       |       |       |       |       |       |       |
   810     820     830     840     850     860     870     880     890     900
gtggcgtcttatgattccactctgatgctgtgatggaaacgtgagcggcgaaagaagcgccacaattgatcgaagcgctcctctataaatggcgagtacc
caccgcagaaatactaaaggtgagactacgactaccttttgcactcgccgctttcttcgcggtgttaactagcttcgcgaggagatattaccgctcatgg >start
                                                                                           |
                                                                                         >TRX_5'F
    |       |       |       |       |       |       |       |       |       |
   910     920     930     940     950     960     970     980     990    1000
gggagggagcctcaagcagtgcctgtcccgttgattcgagtcccgtcctccgcgatttcgtgcaagaagaagagaggaatcgagcgagATGGCGGAGAAAG
ccctccctcggagttcgtcacggaacagggccaactaagctcagggcaggagcgtaaagcacgttcttctctccttagctcgctcTACCGCTCTCTTC

|       |       |       |       |       |       |       |       |       |
  1010    1020    1030    1040    1050    1060    1070    1080    1090    1100
GATCGGTGATCGGGTGCCACACCATCGCCCCAGTGGAACCGGCAGTCCAACTCGCCGGAGCTCCGGAAGCTGgtaaggttccgacttgctcgaccctt
CTAGCCACTAGCCACGGTGTGGTAGCCCGGGGTCACCTTGGCCGTCCGTCGAGGTTGAGCGGCGTCGCTCAGGCCCTTCGACcattccaaggctgaacgagctggaa
                                                                                  INTRON I

|       |       |       |       |       |       |       |       |       |
  1110    1120    1130    1140    1150    1160    1170    1180    1190    1200
tgtgtttgcttctanggttttggggtaaatgtccattgcgacctcgtcatgaaaccaactcttttcttgcactaaaacccngctaaaaccngctaaccngtaaccgtctcct
acacaaacgaagatnccaaaaccccccatttacagtaacgctgagcagtacctttgtggttgagaaaagaacgtgattttgggncgtaaccgtctcct
                                                                                  INTRON I

|       |       |       |       |       |       |       |       |       |
  1210    1220    1230    1240    1250    1260    1270    1280    1290    1300
gctttatatgccgagcttagaatttgagactcagggtttgagtcattcttttatgagttgatattattttctatgctctatctgttgatt
cgaaatatacgcgctcgaatctgaatctgagtcccaaaactcagtgagaaatatcagtaagaaatatctaactatactcaactataataaagatacgagatagacaactaa
                                                                                  INTRON I

|       |       |       |       |       |       |       |       |       |
  1310    1320    1330    1340    1350    1360    1370    1380    1390    1400
tatattggtctaagatcattgttattgtgcaagaatttacagaggaattttacagagaggaataatgacagaaaaagaaggagagtgccatcaaatgctatttgggtgc
ataaccagattctagtaacaataacgttcttaaaatgtctccctttccattactgtctttttctttcctctcacggtagtttacgataaaaccacg
                                                                                  INTRON I
```

Fig. 1B

```
        1410      1420      1430      1440      1450      1460      1470      1480      1490      1500
caagggacaaatttgttctgatgccatgttccattcttgaccctaatgtctaatatcaatggtatctgaattaaacgatgtcattgtgacggtggatgt
                                                          INTRON I
gttccctgtttaaacaagactacggtacaaggtaagaaactggattacagattatagttaccatagacttaattgctacagtaacactgccacctaca 1510      1520      1530      1540      1550      1560      1570      1580      1590      1600
ctaatgtctaagttacagaaacaaaggaggtgtcatcaaatgctattatctggtaattggatgccaaggggcaaattatcatggtgtctaatcaatga
                                                          INTRON I
gattacagattcaatgtctctttgtttcctcccacagtagttacgataatagaccattaacctacggttcccgtttaatagtaccacagattagttact 1610      1620      1630      1640      1650      1660      1670      1680      1690      1700
tatctaatttaaaggctactgcctaaagcccaacctttctcctttattattgttaactcttttattttgaactttttatattctgtgtgtactc
                                                          INTRON I
atagattaaatttccgatgacggatttcgggttggaaagaaggaaataaattaacaattgagaaataaactgaaaatataagacacacatgag <TRX_3'R-3                                                        <TRX_3'R-2
        1710      1720      1730      1740      1750      1760      1770      1780      1790      1800
cacttaattgagcatatcaagttctgtcaaactaagtctatcaaacttttggtggtgaagctgatgattccaagagatcaggaagatctttctattcaac
                                                          INTRON I
gtgaattaactcgtatagttcaagacagtttgattcagataagtagtttgaaaactaaggttcctctagtccttctagaaagataagttg 1810      1820      1830      1840      1850      1860      1870      1880      1890      1900
atccatgtttttttcttatacattgttacaacttagtgttacatcttttcctgtttcataaatgcatatttattttctgaaaaatgtaaagct
                                                          INTRON I
taggtacaaaaagaatatgttaacaatgttgaatcaatgtagaaggacaaagtatttacgtataaataaaagactttttacatttcga 1910      1920      1930      1940      1950      1960      1970      1980      1990      2000
aaacagagtcgaaatctatcaaactgctgcatctcttgttgctctaaagattgtctggtttacagGTGGTCGTAGATTTCACTTCTTCATGGTGTGGT
                                                          INTRON I
tttgtctcagctttagatagtttgacgacgtagagacaaccgagattctaaacagaccaaatgtcCACCAGCATCTAAAGTGAAGAAGTACCACACCA
```

Fig. 1C

```
      2010       2020       2030       2040       2050       2060       2070       2080       2090       2100
CCTTGCCGTATGATTGCCCCGTTCTTCGCGTTCTCTGAGCTAGTAGCTAATAAGTTCACCGATGCCATCTTCCTAAGGTGGACGTCAATGAGCTGAAGgtaaaaacta
GGAACGGCATACTAACGGGGCAAGCGACTCGATCGATTATTCAAGTGGCTACGGTAGAAGATTCCCACCTGCAGTTACTCGACTTCcattttgat
                                                                                                           ^

2110       2120       2130       2140       2150       2160       2170       2180       2190       2200
tcaacatgcagataaactcgtgccgctgttgtttgcgaggtgaaattatgtttctcaacctgtcaccaacgcagAGGGTTGCCCTGGA
agttgtacgtctaatttgagcacggcgacacaacaaacgctccacttaatacaaagattaagaggttggacacagtggtttgccgtcTCCCAACGGGACCT
                                                                                                     ^
                        INTRON II 2210       2220       2230       2240       2250       2260       2270       2280       2290       2300
CTGTGCGATCGAGACACTGCCAACCTTCATCTTCCTGAGGCAGGAGAAACATTGTGGATCGCGTTGTTGTGCTCGTAAAGATCTGTTGCCGAAGAAGATT
GACACGCTAGCTCGTGACGGTTGGAAGTAGAAGGAACTCCGTCCCTTTGTAACACCTAGCCAACACCGAGCATTTCTAGACAACGGCTTCTTCTAA
         <thrdx_3'R                                                                        <TRX_3'UTR 2310       2320       2330       2340       2350       2360       2370       2380       2390       2400
                                                                                      polyA signal
        >stop                                                                           |
          |                                                                           2390
GAGCTCCACATGAGGAACTGAAtgctcgcttgcagtattagtgtcggtgttgggtcgtgaactcggagatttgtgggttagaataacatatgtactg
CTCGAGGTGTACTCCTTGACTTacgagcgaacgtcataatcacagccacaaccagacgcacttgagcctctaaacaccccaatcttatttgtatacatgac 2410       2420       2430       2440       2450
                          polyA signal
                            |
                          2440
aattccatcggttcatgattattaactattgaataactagtctttcatcc
ttaagtagccaagtactaattgataactttatttgatcagaaagtagg
```

Fig. 1D

```
          10         20         30         40         50
GGATCCCAAG ACCCTCGCTC TCTATCTTCG CAACAACTCA CGTCATTGTT

ATTGGTTCCC TTTTTGCCTT CGTCTCAAAT GTCTCATATT GTATAATCTT

CAAGAAGGGT ATTCACGACC TCCTACGATG AAGGAGTGCA CCCTCGTCTG

CTTTCGTTTC TTATCATTGC TTCGTTAGGG AAACATAATA ACTCGGGAAG

GAGACACAAA CAATGTTTAT AGTGATGAGT CATGTAAGGA AGGAGAGAAG

AAAGTTGTGT CGTGATTGCC TCCTTCCCCT TAACCTTTGT TGGATGAAAA

AGATCATTAG GACTCGAAAT TTTAAAGGT GGAGAAGGAG ACCCAAGATA

CCCTCCTCAT AGCAAGATAA GAGATATCCG AGATGAATGT GAGGAAGAAA

ACGATAGCAA ACGATGTAAG TTATCATGAA AATAAAGAGA AATATGAGA

ACCTCATGAT GAGGCTTTAG TGTCACCTCG ATAATTAAAG ACGAGGATAA

CAACGTGACA ACAATAACCA ACAAGGGACA TAAACGATAA AGGCGTTGAT

TGACGAGACC AAAGTCGAAC ATAATAATAT TTTTTTAAGA TAAAAAAAA

AGTAAAAGGA TGTATTTTAG AAGAAAAGAA ATAAAAGATT ATAATTTTTT

TGAGAATTTG TCCGAATACG AATATATATT ATTTTGAATA TTAATTAAAT

AAAGATACCA ACGCGTCGCT TTGGTTCATC GTCTTTCTTT AACGCGGCGG

ACGGGAACGT GAGGCCGACA AAGGTTTCAT GATTCCTAGT GGCGTCTTTA

TGATTTCCAC TCTGATGCTG ATGGAAACGT GAGCGGCGAA AGAAGCGCCA

CAATTGATCG AAGCGCTCCT CTATAAATGG CGAGTACCGG GAGGGAGCCT

CAAGCAGTGC CTTGTCCCGG TTGATTCGAG TCCCGTCCTC CGATTTCGTG

CAAGAAGAGA AGGGAATCGA GCGCCATGG
```

Fig. 2

```
 10         20         30         40         50         60         70         80         90        100
AAAGAAAGAT GTGCAGGTGT TAACCCTTGGT GTTTGATGGA ACACAAGACT CTTTATCAAC AATATGATGA CATTAGAACA AGCAGCTGAC ACGCCATTACT 110        120        130        140        150        160        170        180        190        200
TTTGATCAAG ATAGGCTGCT CTTGATCCCTC TCAGCAGCAG ACAGAATGTA CTTATTCTTG CAATCATGCA GAATGATGTG GCTAAATCAA 210        220        230        240        250        260        270        280        290        300
TACTTTCATT GAACAACTAG AACATGATTT CTCATAAATT TATCGGAAGA TATATAATTA GACTCAAAAC CAGCAGAACA CTACACCAGT TGTTAGTTGC 310        320        330        340        350        360        370        380        390        400
AGCAAAAAAT AATATTGTCA ACAAGAAGCT AGCAGCTATT TACTTCTTCA GCTTCTCCTC AAGCTTCAAG TAAAGGATTT GGGATTGTTC CTAAGAAGGC 410        420        430        440        450        460        470        480        490        500
AGGGCTACTT AATGCGACAT TACCACATGA TATGCATATC TACCCTCTGAA AACTGTTTCC ATGGCTTTCA ATCACATTGT ACTATAAATC TAAGGGAAGA

PEL 1.4>
                                              |
510        520        530        540        550        560        570        580        590        600
AAAGTGCACG CTTTGACTTC GAATTCATTT GTTGACGCTT AGTACATCAA TGGTGTGATC TGCTGCATAC TGCAAGTTGG ATGCAACTTG TAAGAGCTAG 610        620        630        640        650        660        670        680        690        700
AACACGATGG TAGACTGTCA AGCTCTTTGA ATGGGTTTTG CCCTGTGACC ATGGAAAGCT AGAGCGAGAG AGAGGGAGAG AGAGATGACG GTTGGAGAGG 710        720        730        740        750        760        770        780        790        800
AGCCATCACA CTATCCAACA CAATTAGAGG GTGGGCATAA AAAAGGCCAT GTGGGCCGCG AAAAGAGACC TCTCCTTCCC TCCCCCATCG CGTCGCGGAC 810        820        830        840        850        860        870        880        890        900
GGACGGGATC GTCCTAATGT CGTGATCGAC GGCCCACATA CTCACCCGAG ATCGACCGAG GGGCCCACG CCGCGAGGGG AATGGTGGGA AGCTCACGTG 910        920        930        940        950        960        970        980        990       1000
GGAGAAACAT GCGCTGCCGG CCACCTCATC TTCATCATCA ACAGAAACGA GTGGAAGCCC ACCCGCTGAC ATGGCACAAT CGCAGCGGGC TCGATCGATA
```

Fig. 3A

PEL 0.9>

```
         1010       1020       1030       1040       1050       1060       1070       1080       1090       1100
CAAGTCAGGC CGCGCTCTGC GGCCGAAAGC CATCCCATGT GCTGTGCAGT GCCGTGAACA CCCCTATTGT ATCCCTTTCT TCCTTCGCAT GTGTAGTCAC 1110       1120       1130       1140       1150       1160       1170       1180       1190       1200
AGTAACAAGA TCATGACTCC GAATCCATGG AGCTCCTGCA TCTTGGACGA GTTTGGTGTA CCCAAAGAGG ACGCATTGAT GAGCGTGCCG AGATCCCAGG 1210       1220       1230       1240       1250       1260       1270       1280       1290       1300
TATTGGTCAT GGCAATTACC CCCATTCACC TTTGCTAGCA GAGTAATAAC CGTGAATCGG ATGTTAAGTT GCTTAGAGAC TCTTGGGACT TCATCAATGC 1310       1320       1330       1340       1350       1360       1370       1380       1390       1400
TACGGGACCA GATTGAGCCA CAGCACCAAC CTGCGCTTCT CTCTGAAACA AGGCAGTGGT TGGAATGCGC AAACGCCAGC AGTTCAATCT TTCGCTGCAC 1410       1420       1430       1440       1450       1460       1470       1480       1490       1500
TGTCTGCGTC CACAATCCAT TCTGGGGGTT TTCAACTCTG CCTGACACTC GCCATGTGAG GGCTAAAGTT GAGACACCAG CAACAATAAC TGTTCTCCGT 1510       1520       1530       1540       1550       1560       1570       1580       1590       1600
TCCTCGATAA CTTAGGGTTC TCATTCATTA ATGTTCTGGG CAATTCAATT GGCCTCCATG CCCTCTTTCA GCCCTGAGAC AGAGTCTTCT CTGATGTTGT 1610       1620       1630       1640       1650       1660       1670       1680       1690       1700
ACTACCAAAG CTTACTGTAG TATTCATGTCT CTGGTTGTTA AGAAGACAAT TGGCAATGGG AGGTAATGTA TATATGCATC TGAATAATTA 1710       1720       1730       1740       1750       1760       1770       1780       1790       1800
TTCTCTCAGT GTTTTGTTCT TGAGGGCATG GTGGCTTGGT AGTCAAATCT ACCAAAAGAT GAACGGAGAG GAACAGAGTA TGTGTGGAGA AAGGTGCGTC 1810       1820       1830       1840       1850       1860       1870       1880       1890       1900
ACGTTCCCCA TTATCTTTAG CTTCTTAAGAT TCCCCAAATC ACGTACCTTT TTGGACCCCA CCGGCATAGA TTGTTCACAC GACTTCCTCT CTCTTCCTTC 1910       1920       1930       1940       1950       1960       1970       1980       1990       2000
TCTCATCCAT AGCATCCTCT GCCTTTAAAT CCCTTCGTTC CTCTTCCTCT TACTCACAAC TCTCAACTTA CGCTGCCATT TTTGTTCTTA CGGGTGGTCA

2010
GTCCCTTATG
```

Fig. 3B

```
cccgggctgg tagaatggtt ggaatgaaaa aaattatatt ttctcaccgt  -507
tcatatttta taaggtggtg aagaaattat tccaattgaa tatttttttt  -457
gtaattgtgt ggacataata taaatttatg aatatttatg aattgaagaa  -407
aggcaaaggc cacaagaggt gaatgaaagc gatatcataa aaccaaaaaa  -357
cacaaattca attttcaaat ttcaaaaaat tggggctcc aattccaaat   -307
tctcagcaag ccgaagccga gcagaagccg aaaataaaga tccaacggtg  -257
gagattaaag aaatgaaaaa agaggaaaaa gaaaggaaga agaaaggaag  -207
aatggggctg ggaaaggctg tcagccaggt caccctatct tctctggtgg  -157
tcgaaatgat tccttctcca aatttctcat ttccttcgca tttgcatttg  -107
catttgcatt tcccttcttt ccctctctct ctctctctct ctctctctct  -57
ctctctgttt ataaaccccc gtttctcttc ttccctcttc ctcttattct  -7
cgtcttTCAA CTCACCTAGG TCGACAACAC TCACTCCTCT CTCAGCCAGA  +44
CCTTCTTCTT TGGAGGGTTG GCTCTTTCTT CTTCGTTCGT TCCTTCCTTC  +94
CTTCATTCAT TCTCCTCTCT TTCATCCAAG gttgtttctt ccttccctt   +144
ttaccaaat cttctcactt cccttacatt tttcatctgg ggtatcgttc   +194
ttttcccaaa ttatgctgct ttcgtctctc atttatctac tttattgctt  +244
ttaactcatt ttcccttatg cggttcttca attttggctg atcttgctgt  +294
ttgttttgga attctgtttt aatcgccctg gatccgaggt ttttgttcgt  +344
acaatctacc tagattcttt ctgtttgttt gctgatctga aattttccat  +394
ttgggttttg attgtctgtg cttacggaac tgagatctag gatttggagt  +444
tgtgtacctt tttatttctg catgcaattc tgtaatcctg catagctgga  +494
tggctttctg ttgattagtg catgctttgt ttaggacgaa ctgacttgga  +544
ttttttcgttg tcgatctgtt ctattttttg ttttgctgtt ctggttcatg +594
cttggaatga tttagttgct ttgtaaattg tacactctgc ttttgtgtta  +644
gttcacgtag cttctcgatc tgaaattgga tatggttaga gtttatggtc  +694
agcttgtgat cttgcattat gcaaaaattg gaactttaat cctttcatt   +744
tgtaagatct ttaagatatc tgattacctg gttgatttt ttgtgtctgg   +794
attattttat ttgttttgaa agtagtttgt tggttcttcc tgtattattt  +844
gctgaatcgg gatgatcaat tatatgacgt gaatttatgg aatgtaaatg  +894
aatggtttaa gagattgctt tgtgtggctt atttattcaa tttctatttt  +944
tacatcgttt tgtgcagGTT TGAAAAAAA AGGGCCCATG G            +985
```

FIGURE 4

```
          10        20        30        40        50
GGATCCCAAGACCCTCGCTCTCTATCTTCGCAACAACTCACGTCATTGTT 60        70        80        90       100
ATTGGTTCCCTTTTTGCCTTCGTCTCAAATGTCTCATATTGTATAATCTT 110       120       130       140       150
CAAGAAGGGTATTCACGACCTCCTACGATGAAGGAGTGCACCCTCGTCTG 160       170       180       190       200
CTTTCGTTTCTTATCATTGCTTCGTTAGGGAAACATAATAACTCGGGAAG 210       220       230       240       250
GAGACACAAACAATGTTTATAGTGATGAGTCATGTAAGGAAGGAGAGAAG 260       270       280       290       300
AAAGTTGTGTCGTGATTGCCTCCTTCCCCTTAACCTTTGTTGGATGAAAA 310       320       330       340       350
AGATCATTAGGACTCGAAATTTTAAAAGGTGGAGAAGGAGACCCAAGATA 360       370       380       390       400
CCCTCCTCATAGCAAGATAAGAGATATCCGAGATGAATGTGAGGAAGAAA 410       420       430       440       450
ACGATAGCAAACGATGTAAGTTATCATGAAAATAAAGAGAAATATGAGA 460       470       480       490       500
ACCTCATGATGAGGCTTTAGTGTCACCTCGATAATTAAAGACGAGGATAA 510       520       530       540       550
CAACGTGACAACAATAACCAACAAGGGACATAAACGATAAAGGCGTTGAT 560       570       580       590       600
TGACGAGACCAAAGTCGAACATAATAATATTTTTTAAGATAAAAAAAAA 610       620       630       640       650
AGTAAAAGGATGTATTTAGAAGAAAAGAAATAAAGATTATAATTTTTT 660       670       680       690       700
TGAGAATTTGTCCGAATACGAATATATATTATTTTGAATATTAATTAAAT 710       720       730       740       750
AAAGATACCAACGCGTCGCTTTGGTTCATCGTCTTTCTTTAACGCGGCGG
```

FIGURE 5A

```
              760       770       780       790       800
ACGGGAACGTGAGGCCGACAAAGGTTTCATGATTCCTAGTGGCGTCTTTA 810       820       830       840       850
TGATTTCCACTCTGATGCTGATGGAAACGTGAGCGGCGAAAGAAGCGCCA 860       870       880       890       900
CAATTGATCGAAGCGCTCCTCTATAAATGGCGAGTACCGGGAGGGAGCCT 910       920       930       940       950
CAAGCAGTGCCTTGTCCCGGTTGATTCGAGTCCCGTCCTCCGATTTCGTG 960       970       980       990      1000
CAAGAAGAGAAGGGAATCGAGCGCCATGGAAAGgtaaccgcttgatcga
                                 M   E   K 1010      1020      1030      1040      1050
tttgcagcttattgtacggggttttttaactcctgggcttatcgatctgt 1060      1070
cacttgatttttaattagGCCATGG
                  A   M
```

FIGURE 5B

```
AAGCTTGGTA CCGAGCTCGG ATCCCAAGAC CCTCGCTCTT TATCTTCGCA
ACAACTCACG TCATTGTTAT CGGTTCCCCT TTTGCCTTCA TCTCAAATGT     100
CTCATATTGT ATAATCTTCA AGAAGGGTAT TCACGACCTC CTACGATGAA
GGAGTGCACC CTCGCCTGCT TTCGTTTCTT ATCATTGCTT CGTTAGGGAA     200
ACATAATAAC TCGGGAAGGA GACACAAACA ATGTTTATAG TGATGAAGTC
ATGTAAGGAA GGAGAGAAGA AAGTTGTGTC GTGATTGCCT CCTTCCCCTT     300
AACCTTTGGT GGATGAAAAA GATCATTAGG ACTCGAAATT TAAAAGGTGG
AGAAGGAGAC CCAAGATACC CTCCTCATAG CAAGATAAGA GATATCCGAG     400
ATGAATGTGA GGAAGAAAAC GATAGCAAAC GATGTAAGTT ATCATGAAAA
TAAAGAGAAA ATATGAGAAC CTCATGATGA GGCTTTAGTG TCACCTCGAT     500
AATTAAAGAC GAGGATAACA ACGTGACAAC AATAACAAAC AAGGGACATA
AACGATAAAG GCGTTGATTG ACGAGACCAA AGTCGAACAT AATAATATTT     600
TTTTAAGATA AAAAAAAAG TAAAGGATG TATTTTAGAA GAAAGAAAT
AGAAGATTAT AATTTTTTG AGAATTGTC CGAATACGAA TATATATTAT     700
TTTGAATATT AATTAAATAA AGATACCAAC GCGTCGCTTT GGTTCATCGT
CTTTCTTTAA CGCGGCGGAC GGGAACGTGA GGCGGACAAA GGTTTCATGA     800
TTCCTAGTGG CGTCTTTATG ATTTCCACTC TGATGCTGAT GGAAACGTGA
GCGGCGAAAG AAGCGCCACA ATTGATCGAA GCGCTCCTCT ATAAACCCCC     900
GTTTCTCTTC TTCCCTCTTC CTCTTATTCT CGTCTTTCAA CTCACCTAGG
TCGACAACAC TCACTCCTCT CTCAGCCTAG ACCTTCTTCT TTGGAGGGTT     1000
GGCTCTTTCT TCTTCGTTCG TTCCTTCCTT CCTTCCTTCA TTCTCCTCTC
TTTCATCCAA GGTTTGTTTC TTCCTTCCCT TTTTACCAA ATCTTCTCAC     1100
TTCCCTTACA TTTTCATCT GGGGTATCGT TCTTTTCCCA AATTATGCTG
CTTTCGTCTC TCATTTATCT ACTTTATTGC TTTTAACTCA TTTTCCCTTA     1200
TGCGGTTCTT CAATTTTGGC TGATCTTGCT GTTTGTTTTG GAATTCTGTT
TTAATCGCCC TGGATCCGAG GTTTTTAGTT CGTACAATCT ACCTAGATTC     1300
TTTCTAGTTT GTTTGCTGAT CTGAAATTTT CCATTTGGGT TTTGATTGTC
TGTGCTTACG GAACTGAGAT CTAGGATTTG GAGTTGTGTA CCTTTTTATT     1400
TCTGCATGCA ATTCTGTAAT CCTGCATAGC TGGATGGCTT TCTGTTGATT
AGTGCATGCT TTGTTAGGA CGAACTGACT TGGATTTTTC GTTGTCGATC     1500
TGTTCTATTT TTTGTTTTGC TGTTCTGGTT CATGCTTGGA ATGATTTAGT
TGCTTTGTAA ATTGTACACT CTGCTTTTGT GTTAGTTCAC GTAGCTTCTC     1600
GATCTGAAAT TGGATATGGT TAGAGTTTAT GGTCAGCTTG TGATCTTGCA
TTATGCAAAA ATTGGAACTT TAATCCTTTT CATTTGTAAG ATCTTTAAGA     1700
TATCTGATTA CCTGGTTGAT TTTTTTGTGT CTGGATTATT TTATTTGTTT
TGAAAGTAGT TTGTTGGTTC TTCCTGTATT ATTTGCTGAA TCGGGATGAT     1800
CAATTATATG ACGTGAATTT ATGGAATGTA AATGAATGGT TTAAGAGATT
GCTTGTGTG GCTTATTTAT TCAATTTCTA TTTTTACATC GTTTTGTGCA     1900
GGTTTTGAAA AAAAAGGGCC CATGG
```

FIGURE 6

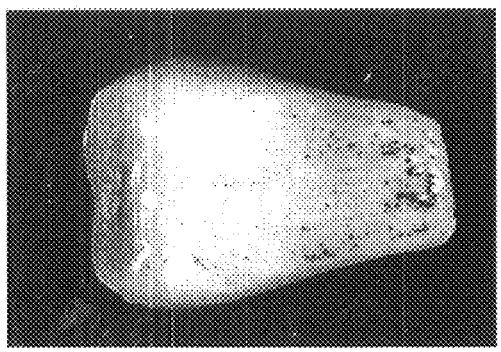
FIG 9A:CaMV35S::GUS
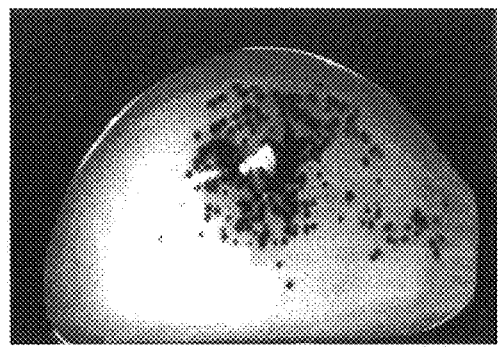
FIG. 9B:CsVMV
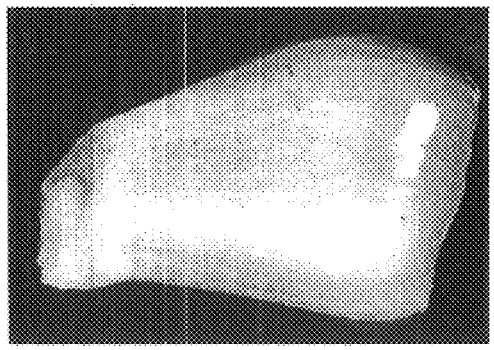
FIG. 9C:RE4
FIG. 9D:Promoterless GUS

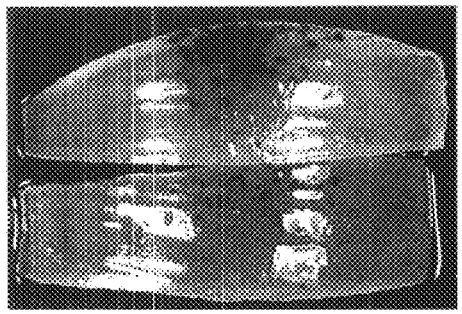
FIG. 10A:CaMV35S::GUS
FIG. 10B:CsVMV
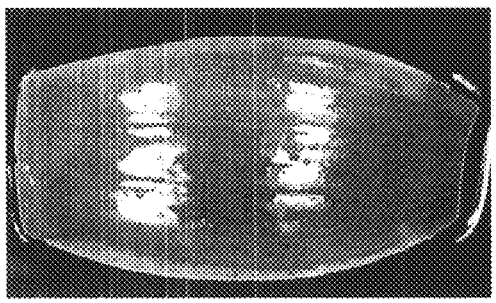
FIG. 10C:RE4
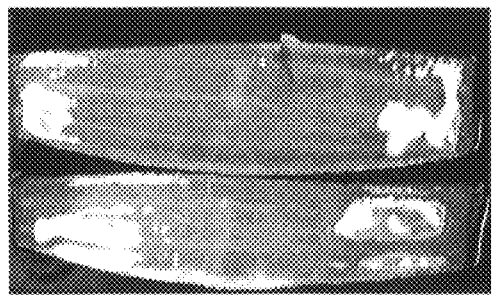
FIG. 10D:Promoterless GUS

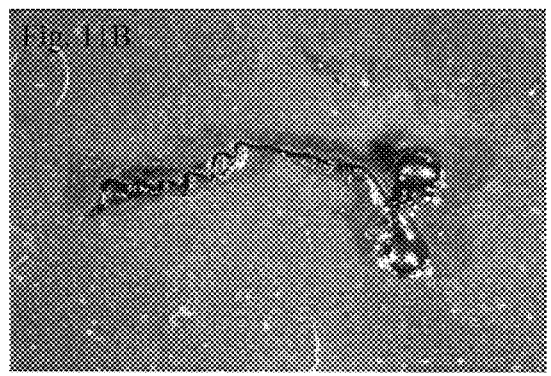
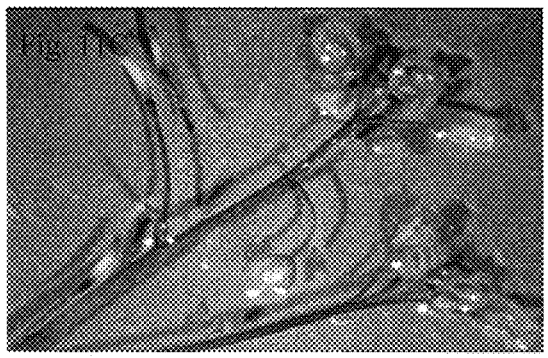
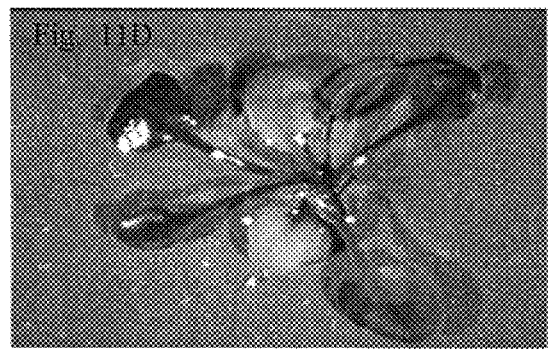

MELON PROMOTERS FOR EXPRESSION OF TRANSGENES IN PLANTS

This application claims priority to U.S. Provisional application Serial No. 60/125,310 filed Mar. 19, 1999 expressly incorporated by reference herein.

Portions of this work were funded by the National Institute of Standards and Technology (NIST) Cooperative Agreement Number 70NANB7H3015. Accordingly, the United States Government has certain rights in this invention.

FIELD OF THE INVENTION

The present invention relates to novel banana fruit-associated promoters, a melon actin promoter and a banana fruit-associated/melon actin fusion promoter. The invention also relates to heterologous nucleic acid constructs, vectors, kits, and transformation methods employing such promoters. The invention further relates to transgenic plant cells and plants transformed with heterologous nucleic acid constructs comprising the promoters and methods for screening plant promoters in various types of plant tissue using a transient expression assay.

REFERENCES

Adams, D. O., and Yang, S. F., *Plant Physiology* 70:117–123 (1977).
Altschul, et al., Nucl. Acids Res. 25(17) 3389–3402 (1997).
An, G, et al., *EMBO J.* 4:277–284 (1985).
An, Y Q et al., *Plant J.* 10(1):107–21 (1996).
Ausubel, F M, et al., in *Current Protocols in Molecular Biology*, John Wiley and Sons, Inc., Media, Pa. (1992).
Ayub, R., et al., *Nature Biotechnology* 14:862–866 (1996).
Becker, D., et al., *Plant Mol. Biol.* 20:1195–1197 (1992).
Bellini, C., et al., *Bio/Technology* 7(5):503–508 (1989).
Bestwick, R K, et al., PCT International Publication No. WO 95/35387, published Dec. 28, 1995.
Brunke, K J and Wilson, S L, European Patent Publication No. 0 559 603 A2, published Sep. 08, 1993.
Clendennen, S K and May, *Plant Physiol.* 115:463–469 (1997).
Comai, L. and Coning, A. J., U.S. Pat. No. 5,187,267, issued Feb. 16, 1993.
Cordes, S, et al., *The Plant Cell* 1:1025–1034 (1989).
Dominguez-Puigjaner et al., *Plant Physiol.* 114:1071–1076 (1997).
Dong, J. Z., et al., *Bio/Technology* 9:858–863, 1991.
Fang, G, and Grumet, R, *Plant Cell Rep.* 9:160–164 (1990).
Ferro, A, et al., U.S. Pat. No. 5,416,250, issued May 16, 1995.
Frisch et al., *Plant Mol. Biol.* 27:405–409, 1995.
Gonsalves, C, et al., *J. Amer. Soc. Hort. Sci.* 119:345–355 (1994).
Hooykaas, P J, and Schilperoot, R A, in *Trends in Biochemical Sciences*, International Union of Biochemistry and Elsevier Science Publishers, v.10(8):307–309 (1985).
Houck, C M and Pear, J R, U.S. Pat. No. 4,943,674, issued Jul. 24, 1990.
Hughes, J A, et al., *J. Bact.* 169:3625–3632 (1987).
Jefferson, R A, et al., *EMBO J.* 6:3901 (1987a).
Jefferson, R A, *Plant Mol. Biol. Rep.* 5:387 (1987b).
Jefferson, R A, *Nature* 342(6251) 837–838, 1989).
Klein, T. M., et al., *PNAS(USA)* 85(22):8502–8505 (1988).
Leisner, S M, and Gelvin, S B, *Proc. Natl. Acad. Sci. USA* 85(8):2553–2557 (1988).
Lin, E et al., *Plant Mol. Biol.* 23:489–499 (1993).
Maniatis, T et al., in *Molecular Cloning: A Laboratory Manual*, Cold Spring Harbor Laboratory, Cold Spring Harbor, N.Y. (1989).
McCormick et al., *Plant Cell Reports* 5:81–84, 1986.
McElroy D, et al., *Plant Mol Biol* 15(2):257–68 (1990).
Medina-Escobar et al., *Plant Mol Biol* 34:867–877 (1997).
Medina-Suarez et al., *Plant Physiol* 115:453–461 (1997).
Miki, B. L. A., et al., *Plant DNA Infectious Agents* (Hohn, T., et al., eds.) Springer-Verlag, Wien, Austria, pp.249–265 (1987).
Ni, M et al., *Plant J.* 7:661–676 (1995).
Norelli et al., *HortScience,* 31:1026–1027, 1996.
Pearson and Meagher, Plant Mol Biol 14(4):513–26, 1990.
Picton, S, et al., *Plant Physiology* 103(4):1471–1472, 1993.
Ranier et al., *Bio/Technology* 8:33–38, 1990.
Robinson, H L and Torres, Calif., *Sem. Immunol.* 9:271–282, 1997.
Rogers, S, U.S. Pat. No. 5,034,322, issued Jul. 23, 1991.
Sagi et al., *Bio/Technology* 5:481–485, 1995.
Sambrook, J, et al., in MOLECULAR CLONING: A LABORATORY MANUAL, Cold Spring Harbor Laboratory Press, Cold Spring Harbor, N.Y., Vol. 2 (1989).
Thomas, *Proc. Natl. Acad. Sci. USA,* 77:5201–5205 (1980).
Tommerup, H, et al., *Eur. Congr. Biotechnol.* 5:916–918 (1990).
Valles, M P and Lasa, J M, *Plant Cell Rep.* 13:145–148 (1994).
Van Haaren, M J J, et al., *Plant Mol. Bio.* 21:625–640 (1993).
Verdaguer et al., *Plant Mol Biol.* 37:1055–1067, 1998
Wang et al., Mol Cell Biol. 12(8):3399–406 (1992).
Yoshioka, K, et al., *Jpn. J. Breeding* 42(2):278–285 (1992).
Zhu, Q, et al., *Plant Cell* 7:1681–1689 (1995).

BACKGROUND OF THE INVENTION

Transcriptional regulatory sequences or promoters that regulate gene expression in plants are essential elements of plant genetic engineering. Several examples of promoters useful for the expression of heterologous genes in plants are now available (Zhu, et al., 1995; Ni, et al., 1995).

Most promoters are from about 500–1500 bases. Promoters for expressing a heterologous gene sequence in plants can be derived from plant DNA, e.g., the cauliflower heat shock protein 80 (hsp80, Brunke and Wilson, 1993; U.S. Pat. No. 5,612,472), or from other sources, for example, plant viruses e.g., the 35S cauliflower mosaic virus promoter, or bacteria which infect plants, e.g., the nopaline synthase (nos) promoter (Rogers, 1991), the octopine synthase (ocs) promoter (Leisner and Gelvin, 1988) and the mannopine synthase (mas) promoter from Agrobacterium.

Expression of heterologous genes or selected sequences of genes in transgenic plants has typically involved the use of constitutive promoters, which drive the expression of a product throughout the plant at all times and in most tissues (e.g., hsp80), the tomato ubiquitin promoter (Picton, et al., 1993), and the raspberry E4 promoter (U.S. Pat. Nos. 5,783,393; and 5,783,394).

A limited number of inducible and/or tissue specific promoters are known. Promoters that provide fruit-specific expression include the E4 and E8 promoter from tomato (Cordes, et al., 1989; Bestwick, et al., 1995; U.S. Pat. No. 5, 859,330). Another fruit-specific promoter is the tomato 2A11 gene promoter. It has been demonstrated that nucleic acid sequences placed under the regulatory control of the 5' non-coding region of the tomato 2A11 gene (Van Haaren, 1993) are preferentially transcribed in developing fruit tissue. Fruit specific regulation of the kiwifruit actinidin promoter has been reported to be conserved in transgenic petunia plants (Lin, et al., 1993).

Pectate lyase (PEL) has been previously identified as fruit- and ripening-associated in banana (Dominguez-Puigjaner et al., 1997; Medina-Suarez et al., 1997), and has recently been associated with breakdown of cell wall components and subsequent fruit softening during strawberry fruit ripening (Medina-Escobar et al., 1997).

Ethylene is a plant hormone influencing many aspects of plant growth and development, and is known to play a major role in the ripening process in fruits and vegetables. A large amount of ethylene is also produced following trauma caused by chemicals, temperature extremes, water stress, ultraviolet light, insect damage, disease, or mechanical wounding. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

In plants, methionine is converted to AdoMet, which is converted to ACC, which is converted to ethylene. AdoMet is synthesized via a condensation reaction between methionine and Adenosine triphosphate (ATP). A bacterial enzyme, AdoMet hydrolase (AdoMetase), which is normally not present in plant tissue, hydrolyzes AdoMet to homoserine and MTA, both of which are recycled to methionine. Plant transformation vectors, tomato fruit-specific promoters and methods of transforming plants with heterologous nucleic acid constructs effective to express AdoMetase (also termed "SAMase") in plant cells and thereby modulate ethylene expression, have been described. See, e.g. co-owned U.S. Pat. Nos. 5,416,250; 5,589,623; 5,723,746; 5,750,864; and 5,859,330, expressly incorporated by reference, herein.

A need exists for constitutive promoters of plant origin and for plant promoters that are functional in fruit, and are capable of providing high level expression of heterologous genes in the cells of fruit.

SUMMARY OF THE INVENTION

Applicants have identified novel banana fruit-associated promoters designated in the present application as "TRX" and "PEL", a melon actin promoter, designated "mACTIN" and melon actin:TRX fusion promoters designated "TRX-intron" and "TRX-actin".

In one embodiment, the invention provides an isolated nucleic acid molecule comprising a banana fruit-associated TRX or "G1A" promoter. In one aspect of this embodiment, the isolated nucleic acid comprises nucleotides 13 to 990 of SEQ ID NO:1 (presented as SEQ ID NO:2), or a functional portion thereof, or is complementary to the nucleic acid sequence, and remains stably bound to it under at least moderate, and optionally, under high stringency conditions.

In another embodiment, the invention provides an isolated nucleic acid molecule comprising a banana fruit-associated PEL promoter. In one aspect of this embodiment, the isolated nucleic acid comprises the sequence presented as SEQ ID NO:3 (FIGS. 3A and B), or a functional portion thereof (e.g., nucleotides 564–2010 or 1099–2010 of SEQ ID NO:3), or is complementary to the nucleic acid sequence, and remains stably bound to it under at least moderate, and optionally, under high stringency conditions In another embodiment, the invention provides an isolated nucleic acid molecule comprising a melon actin promoter designated "mACTIN". In one aspect of this embodiment, the isolated nucleic acid comprises the cDNA sequence presented as SEQ ID NO:4 (FIG. 4), or is complementary to the nucleic acid sequence, and remains stably bound to it under at least moderate, and optionally, under high stringency conditions.

In a related embodiment, the invention provides a TRX-monocot intron and a TRX-actin fusion promoter, designated "TRX-intron" and "TRX-actin, respectively. In one aspect, the isolated nucleic acid comprises the TRX-intron fusion promoter sequence presented as SEQ ID NO:5 (FIGS. 5A–B), or is complementary to the nucleic acid sequence, and remains stably bound to it under at least moderate, and optionally, under high stringency conditions. In another aspect, the isolated nucleic acid comprises the TRX-actin fusion promoter sequence presented as SEQ ID NO:6 (FIG. 6), or is complementary to the nucleic acid sequence, and remains stably bound to it under at least moderate, and optionally, under high stringency conditions.

The invention also provides nucleic acid constructs having a DNA coding sequence under the transcriptional control of a banana fruit-associated promoter, a melon actin promoter, a TRX intron fusion promoter or a banana TRX melon actin fusion promoter. The DNA coding sequence is typically heterologous to the promoter and is operably linked to the promoter to enable expression of the encoded product in plant cells.

In one respect, the banana fruit-associated, TRX-intron and TRX-actin promoters of the present invention can be used to express heterologous genes in a fruit-specific manner. In a related aspect of the invention, such promoters may be used to modulate ethylene production in transformed fruit cells and to thereby alter the ripening phenotype of transgenic fruit comprising such fruit cells.

In another respect, the melon actin promoter of the present invention can be used to express heterologous genes in transformed plant cells, of either dicot or monocot origin.

In a related aspect, the melon actin promoter can be used to consitituitively express heterologous genes in tissue of dicot or monocot plants.

The invention further includes a method for producing a transgenic plant such as a fruit-bearing plant. In this method, the chimeric gene of the present invention, typically carried in an expression vector allowing selection in plant cells, is introduced into progenitor cells of selected plant. These progenitor cells are then grown to produce a transgenic plant bearing fruit.

In a further related embodiment, the invention includes a plant cell, plant tissue, transgenic plant, fruit cell, whole fruit, seeds or calli containing any of the above-described promoters, as well as plant cells comprising the promoters and/or gene products expressed under the control of the promoters.

In another embodiment, the invention provides a transient expression method for evaluating promoter expression in plant tissue. In one preferred aspect of this embodiment, a nucleic acid construct comprising a candidate promoter sequence operably linked to a GUS reporter gene is assembled, plant tissue is prepared for transformation, the nucleic acid construct is introduced into the prepared plant tissue and the plant tissue is cultured under conditions effective and for a time sufficient to detect expression of the transgene.

These and other objects and features of the invention will become more fully apparent when the following detailed description is read in conjunction with the accompanying figures and examples.

BRIEF DESCRIPTION OF THE FIGURES

FIGS. 1A–D show an annotated double-stranded nucleotide sequence, nucleotides 1–2453 (SEQ ID NO:1), of the banana fruit-associated TRX (G1A) gene, containing the nucleotide sequence (SEQ ID NO:2) of the fruit-associated banana TRX promoter. The figure presents the complete sequence of the G1A gene, including the coding sequence (capitalized), the 5'- and 3'-untranslated regions and intron (s) (lower case). Oligonucleotide primer binding sites are indicated above the sequences, a putative TATA box is identified (nucleotide 884), the translational start site is identified (nucleotide 988), the translational stop codon is identified (nucleotides 2319–2321) as are putative polyadenylation signals.

FIG. 2 is a single-stranded depiction of a modified TRX promoter sequence (SEQ ID NO:2), with restriction sites engineered into the 5' and 3' ends, as it occurs in the reporter gene construct pAG 159. A BamHI site (GGATCC) has been engineered into the 5' end, while an NcoI site (CCATGG) has been engineered into the 3' end. The translational start codon consists of the ATG contained within the 3' NcoI site. The putative TATA-box is underlined. FIG. 2 corresponds to nucleotides 13 through 990 of the sequence in FIG. 1, with the exception that restriction sites for BamHI and NcoI have been engineered into the sequence in FIG. 2, at the extreme 5' and 3' ends, respectively.

FIGS. 3A and B are a single-stranded depiction of the 2.0 kb PEL1 promoter sequence (SEQ ID NO:5). The 5' ends of the 1.4 kb and 0.9 kb truncations are indicated in the Figure at approximately nucleotide 564 and nucleotide 1099, respectively. The translation start site (ATG) ending at nucleotide 2010 is in bold type.

FIG. 4 depicts the complete nucleotide sequence of the melon actin promoter ("mACTIN"), up to and including the translational start site. The transcriptional start site, as estimated by characterization of 5'RACE products, is indicated as +1 in the sequence, placing the putative TATA-box at –47.

FIGS. 5A and 5B depict the complete nucleotide sequence of the banana TRX/O2 intron fusion promoter ("TRX-intron" or "TRX-O2intron").

FIG. 6 depicts the complete nucleotide sequence of the banana TRX: melon actin fusion promoter ("TRX-actin"). The TATA-box (nt 890 to 896) is bold-underlined. Restriction sites used in subcloning are underlined, including the NcoI site at the 3' end of the promoter that surrounds the translational start site (ATG).

FIGS. 9A–D illustrate the results of GUS transient assays in garlic (exterior of clove) where GUS expression is driven by (A) the CaMV 35S promoter; (B) the CsVMV promoter; (C) the RE4 promoter; and (D) a promoterless GUS construct.

FIGS. 10A–10D illustrate the results of GUS transient assays in onion (exterior of bulb) where GUS expression is driven by (A) the CaMV 35S promoter; (B) the CsVMV promoter; (C) the RE4 promoter; and (D) a promoterless GUS construct.

FIGS. 11A–D illustrate the results of histochemical staining of untransformed and transformed Arabidopsis tissue at various stages of development, where (A) depicts untransformed Arabidopsis (Col-0 ecotype) at the rosette stage which has no visible blue staining; (B) depicts Arabidopsis seedlings transformed with the mACTIN promoter-reporter gene construct pAG4015, characterized by intense blue staining in all tissues, especially the roots; (C) depicts pAG4015 transformed Arabidopsis at the rosette stage which has more intense blue staining in the cotyledons, early true leaves and roots than in the later developing leaves; and (D) depicts pAG4015 transformed Arabidopsis at the flowering stage which has an intense blue staining in the stem and less intense blue staining in the flowers and siliques which have blue staining at the base and the tip.

DETAILED DESCRIPTION OF THE INVENTION

I. Definitions

Figure 7:
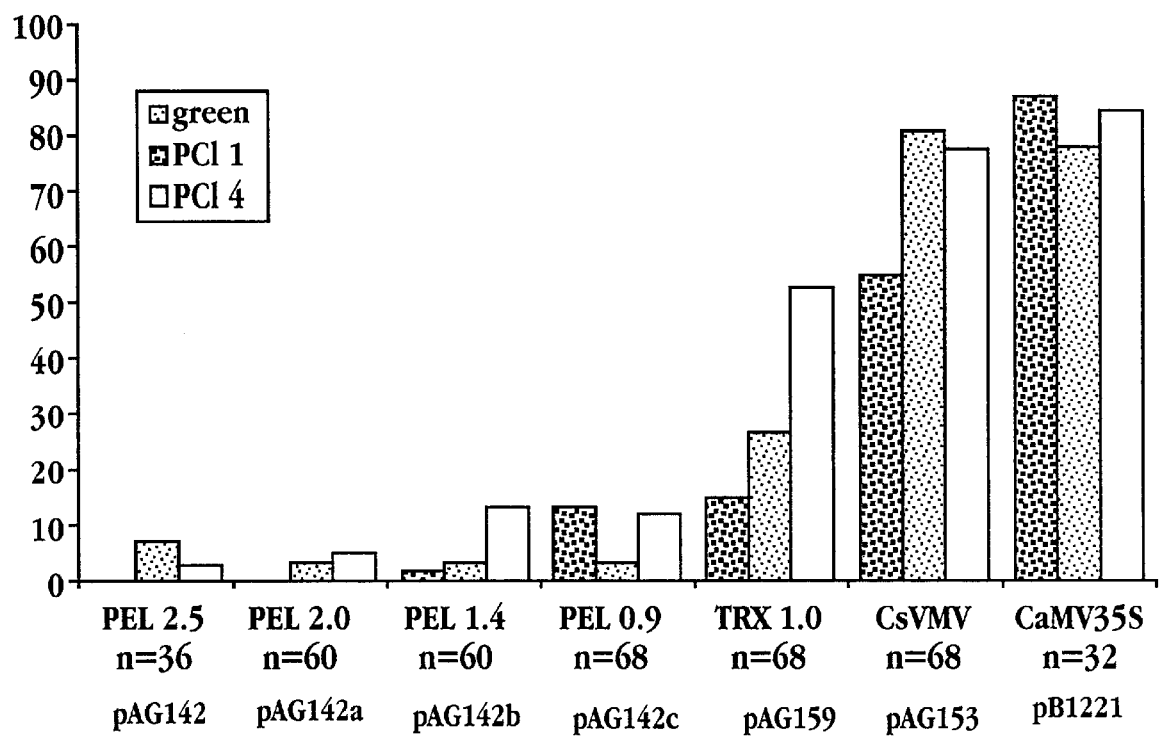
FIG. 7 illustrates the results of GUS reporter assays with the PEL 2.0 kb (pAG142a), PEL 1.4 kb (pAG142b), PEL 0.9 kb (pAG142c), TRX 1.0 (pAG159), and CsVMV promoters (pAG153), in edible banana pulp at green, PCl 1 and PCl 4 stages of ripening, presented as the percentage of fruit slices with GUS foci.

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

A nucleic acid may be double stranded, single stranded, or contain portions of both double stranded and single stranded sequence. The depiction of a single strand also defines the sequence of the other strand and thus also includes the complement of the sequence which is depicted.

As used herein, the term "recombinant nucleic acid" refers to nucleic acid, originally formed in vitro, in general, by the manipulation of nucleic acid by endonucleases, in a form not normally found in nature.

As used herein, the terms "chimeric gene construct" and "chimeric nucleic acid construct" are used interchangeably and refer to recombinant nucleic acid sequences which comprise a nucleic acid coding sequence and control sequences required for expression of the coding sequence in a plant cell.

As used herein, the term "regulatable promoter" refers to any promoter whose activity is affected by specific environmental or developmental conditions (e.g., a tomato E4 or E8 promoter).

As used herein, the term "constitutive promoter" refers to any promoter that directs RNA production in many or all tissues of a plant transformant at most times.

As used herein, the term "tissue-associated promoter" refers to any promoter which directs RNA synthesis at higher levels in particular types of cells and tissues (e.g., a fruit-associated promoter);

As used herein, the terms "promoter" or "promoter segment" refer to a sequence of DNA that functions in a promoter disclosed herein to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start.and stop sequences, and enhancer or activator sequences.

By "plant promoter" is meant a promoter or promoter region (as defined above), which in its native form, is derived from plant genomic DNA. The banana fruit-associated promoters of the present invention are plant promoters.

Alternatively, a fruit-associated TRX promoter is obtained from the gene encoding a banana TRX protein, wherein the gene encoding the fruit-associated TRX protein preferably has at least about 70%, more preferably about 80%, and even more preferably about 85 to 90% sequence identity over a length of nucleic acid sequence corresponding to the banana TRX gene sequence of SEQ ID NO:1. Using techniques routinely employed by on those of skill in the art, once the gene encoding a fruit-associated TRX protein is identified based on sequence identity, the associated fruit-associated TRX promoter is readily identified using conventional genome walking techniques (i.e., the Universal Genome Walker Kit, Clontech Laboratories, Inc., Palo Alto, Calif.).

As used herein, "promoter strength" refers to the level of promoter-regulated expression of a heterologous gene in a plant tissue or tissues, relative to a suitable standard (e.g., a fruit-associated promoter from a particular plant, e.g., banana, versus a control or standard gene promoter, e.g., the 35S CaMV promoter or the CsVMV promoter (cassava vein mosaic virus promoter, Verdaguer et al., 1998). Expression levels can be measured by linking the promoter to a suitable reporter gene such as GUS (β-glucuronidase). Expression of the reporter gene can be easily measured by fluorometric, spectrophotometric or histochemical assays (Jefferson, et al., 1987a; Jefferson, 1987b; Jefferson, R A, 1989).

A "heterologous" nucleic acid construct or sequence has a portion of the sequence which has been introduced into the plant cell in which it is expressed. Heterologous, with respect to a control sequence may refer to a control sequence (i.e. promoter or enhancer) that does not function in nature to regulate the same gene the expression of which it is currently regulating. Generally, heterologous nucleic acid are introduced into the cell or part of the genome in which they are present, and have been added to the cell, by transfection, microinjection, electroporation, or the like. The sequences may contain a control sequence/coding sequence combination that is the same as, or different from a control sequence/coding sequence combination found in the native plant.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

The term "gene", may be used interchangeably herein with the term "heterologous nucleic acid coding sequence", and the term "structural gene" means a DNA coding region.

As used herein, the term "sequence identity" means nucleic acid or amino acid sequence identity in two or more aligned sequences, aligned using a sequence alignment program. Sequence searches are preferably carried out using the BLASTN program when evaluating the of a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

The term "% homology" is used interchangeably herein with the term "% identity" herein and refers to the level of identity between two sequences, i.e. 70% homology means the same thing as 70% sequence identity as determined by a defined algorithm, and accordingly a homologue of a given sequence has at least about 70%, preferably about 80%, more preferably about 85%, even more preferably about 90% sequence identity over a length of the given sequence.

A preferred alignment of selected sequences in order to determine "% identity" between two or more sequences, is performed using the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate stringency hybridization and wash conditions. Exemplary conditions include hybridization conducted as described in the Bio-Rad Labs ZetaProbe manual (Bio-Rad Labs, Hercules, Calif.), expressly incorporated by reference herein. For example, hybridization is conducted in 1 mM EDTA, 0.25 M $Na_2HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Hybridization conditions are further recited in Ausubel FM et al., 1993, expressly incorporated by reference herein.

As used herein, the term "expression" refers to the process by which a polypeptide is produced based on the nucleic acid sequence of a gene. The process includes both transcription and translation.

As used herein, the terms "transformed", "stably transformed" or "transgenic" refer to a plant cell that has a non-native (heterologous) nucleic acid sequence integrated into its genome which is maintained through two or more generations.

As used herein, the term "modulate" refers to a change in biological activity. Modulation may relate to an increase or a decrease in biological activity, binding characteristics, or any other biological, functional, or immunological property of the molecule.

As used herein, the term "ethylene regulated", refers to regulation which is induced by changes in ethylene concentration in the plant. For example, promoter activity which occurs or primarily occurs, during later stages of fruit development and/or early stages of fruit ripening, is said to be ethylene regulated.

As used herein, a "plant cell" refers to any cell derived from a plant, including undifferentiated tissue (e.g., callus) as well as plant seeds, pollen, progagules and embryos.

II. Isolation and Characterization of Banana Fruit-Associated Promoters

Several cDNA fragments were identified as being fruit-associated and abundantly expressed in banana by differential display. Analysis of fruit-associated differential display fragments together with PCR amplification of genomic DNA with oligonucleotide primers complimentary to conserved regions of known sequences led to the eventual identification and characterization of the promoter sequences described herein.

A. Isolation and Characterization of a Banana Fruit-Associated TRX Promoter

Differential display was performed using total banana RNA from pulp, root, corm, and leaf of greenhouse-grown plants, and in vitro plantlets (root and shoot), to identify RNA fragments differentially and abundantly expressed in banana, as described in Example 1. Analysis of 36 fruit-associated differential display fragments led to the eventual selection of a sequence for promoter isolation and characterization (G1A).

One of the fragments, G1A, was hybridized to RNA from banana pulp at different stages of ripening. The G1A transcript was found to increase with fruit ripening. When hybridized to a banana genomic Southern blot, G1A was found to be represented by a small gene family in banana.

When differential display was performed using total banana RNA from pulp with the G-anchored primer (H-T$_{11}$G, SEQ ID NO:15) used for the amplifications, along with arbitrary primers, H-AP1 through H-AP8 (SEQ ID NOs:7–14; GenHunter Corp., Nashville, Tenn.), several amplified differential display products were found to be unique to pulp and undetectable in root, corm, leaf, or in vitro plantlet tissue, as described in Example 1. Among these were an approximately 400 bp product using the H-AP1 primer (SEQ ID NO: 7; GenHunter Corp., Nashville, Tenn.).

The recovered differential display product was used as a probe on Northern blots to confirm tissue distribution of the associated transcript. Results from Northern blot analysis using G1A as a probe indicate that the native transcript is approximately 600 nt, and highly fruit-associated (not detected in any other tissue analyzed including root, corm, leaf, or in vitro plantlet). When the G1A transcript was hybridized to RNA from banana pulp at different stages of ripening, it was barely detectable in green bananas not treated with ethylene, and the transcript abundance increased dramatically after ethylene treatment and during ripening.

Following cloning, the differential display products were sequenced and compared to sequences available in GenBank, using a basic BLASTN search of non-redundant nucleic acid sequence databases through NCBI (http://www.ncbi.nlm.nih.gov/index.html), using default parameters and G1A (TRX) was found to display significant sequence similarity to other plant thioredoxin genes.

The sequences for many plant thioredoxin genes were found in GenBank. The coding sequence of banana G1A, designated herein as TRX, is 58.6% (280 out of 478 nucleotides) identical at the nucleotide level to its closest neighbor, wheat thioredoxin (TRX), Accession AJ009762. Outside of the coding sequence, which includes the TRX promoter, no significant matches between the banana sequence and any other sequence in GenBank was detected using the BLASTN program with default parameters.

Thioredoxin is known to exist in higher plants in several forms. The m and f isoforms are chloroplastic, whereas the h isoform is cytosolic and lacks both a signal and transit sequence. Two wheat thioredoxin genes have recently been characterized and appear to contain a transmembrane domain at the N-terminus, indicating a membrane association. The coding sequence associated with the banana thioredoxin described herein is most similar to the h isoform, and lacks any apparent presequence, suggesting that it cytosolic.

Thioredoxin h genes generally exist as small gene families in higher plants, although at least five putative sequences have been characterized in Arabidopsis. Both wheat and tobacco have two closely related thioredoxin h genes that are differentially expressed. Prior to the present invention, a fruit-associated thioredoxin had not been reported.

Upstream sequences associated with the TRX banana differential display product were isolated in a series of steps, as detailed in Example 1. The upstream sequences were isolated by genome walking an assembled into a contiguous sequence (FIGS. 1A–D).

A Basic BLASTN search (http://www.ncbi.nlm.nih.gov/BLAST/) of non-redundant nucleic acid sequence databases through NCBI (http://www.ncbi.nlm.nih.gov/index.html) revealed no significant matches to the TRX promoter presented in FIG. 2.

A modified promoter sequence, with restriction sites engineered into the 5' and 3' ends was constructed for incorporation into the pAG 159 reporter gene construct, as described below in Example 1.

B. Isolation and Characterization of a Banana Fruit-Associated PEL Promoter

Pectate lyase (PEL) was previously associated with fruit and ripening in banana (Dominguez-Puigjaner et al., 1997; Medina-Suarez et al., 1997), and with the breakdown of cell wall components and subsequent fruit softening during strawberry fruit ripening (Medina-Escobar et al., 1997). Two banana and one strawberry pectate lyase cDNA sequences may be found in GenBank at Accession numbers X92943, Z93106 and U63550, for PEL1, PEL2 and strawberry PEL, respectively.

The expression of pectate lyase in banana fruit is coordinated with ripening and can be stimulated by exogenous ethylene (Dominguez-Puigjaner et al, 1997.) However, the tissue distribution of the PEL transcript has not been previously reported.

PCR amplification of banana genomic DNA with oligonucleotide primers complimentary to conserved regions of the PEL coding sequence yielded two different-sized products (PEL1 and PEL2), which were cloned, sequenced, and used to design gene-specific oligonucleotide primers. Results of semi-quantitative reverse transcriptase polymerase chain reaction (RT-PCR) using cDNA from ripe banana pulp as a template indicated that the PEL1 transcript was more abundant in ripe banana pulp than the PEL2 transcript.

Alignment of the two banana PEL sequences with the PEL sequences in GenBank indicated that PEL1 (GenBank accession number X92943), has the same coding sequence as described by Dominguez-Puigjaner et al., 1997, and that PEL2 (GenBank accession number Z93106), has the same coding sequence as described by Medina-Suarez et al, 1997. A search GenBank for related sequences indicated one additional fruit-associated pectate lyase isolated from Strawberry (Medina-Escobar et al., 1997).

Alignment of the two banana PEL coding sequences and the strawberry PEL coding sequence from GenBank using MacVector version 6.5, revealed sequence regions which are conserved between the three fruit-associated pectate lyases. PEL promoter sequences were identified in a multi-step process, and prior to the present invention, the promoter sequence for PEL had not been reported.

A cDNA library was generated and adaptors ligated to double-stranded cDNA in order to provide a PCR-accessible library for rapid amplification of cDNA 5' or 3' ends (5' or 3' RACE, respectively), as detailed in Example 2, below. A putative promoter fragment of approximately 2.5 kb was amplified from the ScaI digested genomic banana library, cloned and completely sequenced.

The PEL1 2.5 kb promoter fragment was subcloned as a translational fusion with GUS in a reporter gene construct, then truncated at the 5' end to generate promoter fragments 2.0 kb (SEQ ID NO:3) and truncations thereof 1.4 kb, and 0.9 kb as described in Example 2. See, also FIGS. 3A and 3B. The various PEL promoter fragments were incorporated into reporter constructs in translational fusion with a GUS sequence, also described in Example 2.

III. Melon Actin Promoter

Actin is a ubiquitously expressed protein that is an integral component of the cytoskeleton. Because of its high degree of conservation and abundant expression in almost every eukaryotic tissue, actin has become a common standard or control gene in the study of biological systems. Actin expression is generally considered to be both ubiquitous and constitutive and actin sequences and gene structure are well-conserved among plants. In plants, functional actin genes are commonly comprised of five exons interrupted by four introns. The intron positions are well conserved among plants and are rather small, although the intron length and sequence are variable. See, e.g., Pearson and Meagher, 1990, soybean actin; An et al., 1996, Arabidopsis actin; and McElroy et al., 1990, rice.

The isolation and characterization of a genomic DNA fragment upstream of a melon (*Cucumis melo*) actin coding sequence is described herein and identified as the melon actin promoter ("mACTIN", Example 3). The MACTIN promoter sequence (SEQ ID NO:4) is derived from a dicot, however, it exhibits surprisingly strong constitutive promoter activity in both monocots and dicots. Although the promoter is of plant origin, it exhibits a level of promoter activity that is similar to the commonly used CaMV viral promoter.

IV. Melon Actin:Banana Fruit-Specific TRX Fusion Promoters

The banana fruit-specific TRX promoter exhibited a moderate level of activity as determined by transient reporter gene activity in banana fruit slices. Two modified forms of the promoter were constructed by (1) adding a monocot intron to the 3' end of the banana TRX promoter and (2) by fusing the banana TRX promoter with the melon actin promoter at the TATA-box.

The melon actin promoter is a strong constitutive promoter that is active in both monocots and dicots and does contain an intron in the 5' untranslated leader. While the mechanism is not part of the invention, it was predicted that the addition of an intron in the 5' untranslated leader to the banana TRX promoter would increase the activity of the banana TRX promoter, but that the fruit-specificity of the TRX promoter would remain unchanged since the functional elements controlling tissue specificity are predicted to occur upstream of the TATA-box.

The construction and evaluation of a TRX-melon actin and a TRX-monocot intron fusion promoter is further described in Example 4. According to the results of transient expression assays using the modified TRX promoters, the fusion promoters demonstrate improved performance relative to the banana fruit-specific TRX promoter in transient expression assays.

V. Vectors for Transforming Plant Cells

The present invention provides vectors suitable for the transformation of plants. The vectors, chimeric genes and DNA constructs of the present invention are also useful for the expression of heterologous genes. Transgenic plants, transgenic plant cells and transgenic fruit, carrying the chimeric genes of the present invention, may be a useful source of recombinantly-expressed material.

The banana fruit-associated and TRX fusion promoters of the invention find utility in chimeric gene constructs for the fruit-associated expression of heterologous structural genes operably linked to a promoter. The methods and results described herein are directed to fruit-associated gene expression under the control of the banana fruit-associated and TRX fusion promoters of the invention, as well as consitituitive gene expression under the control of the melon actin promoter in transgenic plant cells. The promoters of the invention include a region of DNA that promotes transcription of a gene operably linked thereto, in transformed plant cells.

Using known, routine DNA manipulation techniques such as those described in Sambrook et al. (1989), heterologous gene constructs can be made whereby a foreign structural DNA sequence of interest, or gene, can be placed under the regulatory control of a banana fruit-associated promoter of the invention.

The construction of expression vectors or heterologous gene constructs suitable for transformation techniques into plants is known to those of ordinary skill in the art. (see, for example, Houck and Pear, 1990, and Becker, et al., 1992).

For expression in plants, the expression vectors of the invention may be constructed to containing an insertion site for a DNA coding sequence of interest. The transcription of such inserted DNA is then under the control of a banana fruit-associated promoter of the invention.

Such expression vectors may have single or multiple transcription termination signals at the 3' end of the DNA sequence being expressed. The expression cassette may also include, for example, (i) a DNA sequences encoding a leader sequence (e.g., to allow secretion or vacuolar targeting), (ii) translation termination signals, (iii) selectable marker genes for use in plant cells, (iv) sequences that allow for selection and propagation in a secondary host, such as an origin of replication and a selectable marker sequence.

Selectable marker genes encode a polypeptide that permits selection of transformed plant cells containing the gene by rendering the cells resistant to an amount of an antibiotic that would be toxic to non-transformed plant cells. Exemplary selectable marker genes include the neomycin phosphotransferase (nptII) resistance gene, hygromycin phosphotransferase (hpt), bromoxynil-specific nitrilase (bxn), phosphinothricin acetyltransferase enzyme (BAR) and the spectinomycin resistance gene (spt), wherein the selective agent is kanamycin, hygromycin, geneticin, the herbicide glufosinate-ammonium ("Basta") or spectinomycin, respectively.

Typical secondary hosts include bacteria and yeast. In one embodiment, the secondary host is *Escherichia coli*, the origin of replication is a colE1-type, and the selectable marker is a gene encoding ampicillin resistance. Origin of replication and selectable marker sequences operative in secondary hosts are well known in the art and many are commercially available (e.g., Clontech, Palo Alto, Calif.; Stratagene, La Jolla, Calif.). The vectors of the present invention are useful for fruit tissue-associated expression (using a banana TRX or PEL promoter, a TRX-intron or a TRX actin fusion promoter) or constituitive expression (mACTIN) of nucleic acid coding sequences in plant cells. For example, a selected peptide or polypeptide coding sequence can be inserted in an expression vector of the present invention. The vector is then transformed into host cells, and the host cells cultured under conditions to allow the expression of the protein coding sequence. In some cases, the expressed peptide or polypeptide is isolated from the cells. Transformed plant progenitor cells can also be used to produce transgenic plants bearing fruit.

Further, the invention includes a method for producing a transgenic fruit-bearing plant, where fruit produced by the plant has a modified phenotype. In this method a heterologous gene construct is introduced (e.g., by transformation) into progenitor cells of the plant. An exemplary heterologous gene construct is composed of (i) a DNA sequence encoding a gene product effective to modify a phenotypic characteristic of the plant, e.g., to reduce ethylene biosynthesis in fruit produced by the plant, operably linked to (ii) a banana or TRX fusion promoter of the invention wherein expression is fruit-associated. In another embodiment, the invention includes a method for producing a transgenic plant, where an exemplary heterologous gene construct is composed of (i) a DNA sequence encoding a transgene product, operably linked to (ii) a melon actin promoter wherein expression is constituitive.

The DNA sequence is heterologous to the promoter and the chimeric gene contains the appropriate regulatory elements necessary for expression in a plant cell. Transformed progenitor are grown to produce a transgenic plant bearing fruit. The method further includes transforming progenitor cells of the plant with a vector containing a selectable marker and the heterologous gene.

It will be understood that the vectors described herein may form part of a plant transformation kit. Other components of the kit may include, but are not limited to, reagents useful for plant cell transformation.

VI. Methods of Transforming Plant Cells

Chimeric genes containing a banana fruit-associated promoter of the invention, e.g., TRX or PEL, a melon actin promoter of the invention, a TRX:intron or a TRX:melon actin fusion promoter of the invention, can be transferred to plant cells by any of a number of plant transformation methodologies, including Agrobacterium-based methods [Ranier et al., 1990 (rice); McCormick et al., 1986 (tomato); Norelli et al., 1996 (apple)], electroporation, microinjection, and microprojectile bombardment. (See, e.g., Comai and Coning, 1993; Klein, et al., 1988; Miki, et al. 1987; Bellini, et al., 1989).

In one embodiment, chimeric genes are introduced into plants by way of a T-DNA-less Ti plasmid carried by *Agrobactenium tumefaciens*, followed by co-cultivation of the *A. tumefaciens* cells with plant cells. In such cases, vectors for use in the invention contain a selectable marker gene, T-DNA border regions from *Agrobacterium tumefaciens*, a heterologous gene of interest, and other elements as desired. Exemplary Agrobacterium transformation vectors are commercially available from Clontech (Palo Alto, Calif.) and further described by An, et al., 1985.

Other suitable vectors may be constructed using the promoters of the present invention and standard plant transformation vectors, which are available both commercially (Clontech, Palo Alto, Calif.) and from academic sources [Salk Institute, Plant Biology Labs; Texas A & M University (Frisch et al., 1995); Waksman Institute, Rutgers, The State University of New Jersey, Piscataway, N.J.].

Another embodiment is based on microprojectile bombardment using microparticles loaded with DNA which are bombarded into the cells using "gene gun" technology. (See, e.g., Robinson, H L and Torres, Calif., 1997.)

When electroporation or microprojectile bombardment transformation techniques are utilized, the transformation vector generally contains the heterologous gene of interest and a selectable marker gene construct to determine whether the transformation event was successful.

Transformed plant cells are obtained as a result of the transformation of the plant cells with a heterologous gene construct containing a promoter of the invention operably linked to a heterologous gene. The plant cells are cultured in medium containing the appropriate selection agent to identify and select for plant cells which express the chimeric gene. After plant cells that express the chimeric gene are selected, whole plants are regenerated from the transgenic plant cells. Techniques for regenerating whole plants from transformed plant cells are known in the art. Suitable plant regeneration protocols are also known.

The invention further includes a method for producing a transgenic plant such as a fruit-bearing plant. In this method, the chimeric gene of the present invention, typically carried in an expression vector allowing for selection in plant cells, is introduced into progenitor cells of a plant. These progenitor cells are then grown to produce a transgenic plant bearing fruit.

Preferred plants suitable for transformation using the banana fruit-associated, melon actin and TRX fusion promoters of the invention, and include but are not limited to, banana, tomato, pineapple, grape, raspberry, strawberry, kiwi fruit, avocado, melon, mango, papaya, apple, peach, pear, cherry, citrus, date palm, plantain, soybean, cotton, alfalfa, oilseed rape, flax, sugar beet, sunflower, potato, tobacco, maize, wheat, rice, nuts and lettuce.

In one exemplary embodiment, cotyledon explants of a commercial cantaloupe variety (Cucumis Melo, Muskmelon) are transformed according to known methods (Fang and Grumet, 1990; Valles and Lasa, 1994; Dong, et al., 1991; Gonsalves, et al., 1994; Yoshioka, et al., 1992; Ayub, et al., 1996), using the a disarmed Agrobactefium strain to introduce the above-described binary vectors into plants. The disarmed Agrobacterium strain is co-cultivated with melon cotyledon tissue explants, and primary transformants selected on the basis of their capacity to regenerate and develop roots on media containing the antibiotic, kanamycin.

In other exemplary embodiments, Agrobacterium transformation methods as described for banana, rice, tomato, apple are used to transform plant cells using a promoter of the invention. Agrobacterium transformation has been previously described for rice, tomato, apple, almond, asparagus, avocado, broccoli, carrot, cauliflower, celery, cucumber, grape, persimmon, and spinach. See, e.g., Sagi et al., 1995 (banana); Ranier et al., 1990 (rice); McCormick et al., 1986 (tomato), Van Eck J M, et al., Plant Cell Reports 14: 299–304, 1995 (tomato); Norelli et al., 1996 (apple); Miguel C M et al., Plant Cell Reports 18: 387–93, 1999 (almond);

Cabrera-Ponce J L et al., Plant Cell Reports 16: 255–260, 1997, Delbreil B et al., Plant Cell Reports 12:129–132, 1993 (asparagus); Mogilner N et al., Mol Plant Microbe Interact 6(5):673–5, 1993 (avocado); Hosoki T et al., J. Japan Soc. Hort. Sci. 60: 71–75, 1991 (broccoli); Hardegger M et al., Molecular Breeding 4: 119–127, 1998 (carrot); Bhalla P L and Smith N, Molecular Breeding 4: 531–41, 1998 (cauliflower); Catlin D et al., Plant Cell Reports 7: 100–103, 1988 (celery); Sarmento G G et al., Plant Cell Tissue and Organ Culture 31: 185–193, 1992 and Trulson A J et al., Theor Appl Genet 73: 11–15, 1986 (cucumber); Scorza R et al., Plant Cell Reports 14: 589–92, 1995 and Franks T et al., Molecular Breeding 4:321–33, 1998 (grape); Nakamura Y et al., Plant Cell Reports 17:435–440 (persimmon); and Zhang HX and Zeevaart JAD, Plant Cell Reports 18: 640–45, 1999 (spinach).

VII. Heterologous Genes

Any structural gene of interest may be placed under the regulatory control of a promoter of the invention. The structural gene may encode for a polypeptide of interest or other gene product.

According to methods of the present invention, heterologous genes may be operably linked to a banana fruit-associated, melon actin or TRX fusion promoter of the invention.

In one respect, the banana fruit-associated promoters of the invention are used to modulate ethylene production in transformed fruit cells, and thereby alter the ripening and delay senescence of transgenic fruit composed of such fruit cells.

In this embodiment of the invention, the promoters described herein are employed in a method for prolonging ripening and delaying senescence of fruit from a fruit-bearing plant, e.g., banana. In this aspect of the invention, transgenic plant cells containing the promoters of the present invention are grown to produce a transgenic plant bearing fruit.

In particular, plant cells are transformed with a heterologous nucleic acid construct encoding a product capable of reducing ethylene biosynthesis when expressed in plant cells (e.g., S-adenosyl-methionine hydrolase (SAMase, Ferro et al., 1995; Hughes et al., 1987), aminocyclopropane-1-carboxylic acid (ACC) deaminase, ACC oxidase antisense molecule, ACC synthase antisense molecule, ACC oxidase cosuppression molecule, ACC synthase cosuppression molecule), which is under the control of a banana promoter of the invention. Fruit produced by these transgenic plants have a modified ripening phenotype, as described in co-owned U.S. Pat. Nos. 5,859,330; 5,783,394; 5,783,393; 5,723,746; 5,589,623; 5,416,250 and 5,750,864, expressly incorporated by reference herein.

A modified ripening phenotype refers to an alteration in the rate of ripening; characterized by an increased ripening time course, or prolonged ripening and the delayed senescence of, a transgenic fruit relative to corresponding (i.e., non-transgenic) wild-type fruit.

In another embodiment, the nucleic acid coding sequence can correspond to a pathogenesis related gene, such as polygalacturonase inhibiting protein (PGIP), glucanase and chitinase.

In further embodiments, the nucleic acid coding sequence includes sequences which affect: (i) flavor (e.g., thaumatin; GenBank); (ii) pigmentation (e.g., products that modify lycopene synthesis, such as lycopene cyclase; GenBank); (iii) enzymes or other catalytic products (such as, ribozymes or catalytic antibodies) that modify plant cell processes; (iv) enzymes that inhibit degradation of ripened fruit (e.g., antisense polyphenol oxidase and antisense polyphenol peroxidase (to inhibit browning) and antisense pectate lyase (to inhibit softening); (vi) antimicrobial peptides, (vii) sucrose accumulating genes, such as the sucrose phosphate synthase gene (GENBANK) and (viii) genes which affect the metabolism of sucrose (e.g., invertase).

VIII. Identification and Evaluation of Transformants

Following transformation, transgenic plant cells are assayed for expression of a transgene which is operably linked to a banana fruit-associated, melon actin or TRX fusion promoter of the invention. Transgenic plant cells may be initially selected by their ability to grow in the presence of a selective agent, such as the aminoglycoside antibiotic, kanamycin.

Expression of a transgene may also be determined by analysis of DNA, mRNA, and protein, associated with the expression of the transgene. The assays are typically conducted using various plant tissue sources, e.g., leaves, stem, or fruit.

A. Construction of Plant Transformation Vectors and Evaluation of Reporter Expression Banana Fruit-Associated Promoters The relative activity of the banana fruit-associated promoters of the invention was evaluated in a transient assay system using a reporter gene, exemplified by GUS ($\beta$-glucuronidase), effective to evaluate the tissue-associated regulatable expression from the promoters Expression of GUS protein is easily measured by fluorometric, spectrophotometric or histochemical assays (Jefferson, 1987a).

The results of functional assays of the fruit-associated promoters PEL and TRX in GUS reporter gene constructs, suggests that the PEL and TRX sequences function as promoters in fruit tissue, are ethylene responsive and associated with ripening.

Recombinant nucleic acid constructs comprising; pAG142a-pel::GUS (2.0 kb), pAG142b-pel::GUS (1.4 kb), pAG142c-pel::GUS (0.9 kb), pAG153-CsVMV::GUS, pAG159-TRX::GUS and pBI221-35S::GUS were prepared using the isolated promoter sequences and techniques routinely employed by those in the art, then introduced into banana plant cells by particle bombardment, as described below in Examples 1 and 2.

The promoter activity of various recombinant nucleic acid constructs, pAG142a-pel::GUS (2.0 kb), pAG142b-pel::GUS (1.4 kb), pAG142c-pel::GUS (0.9 kb), pAG153-CsVMV::GUS, pAG159-TRX::GUS and PBI221-35S::GUS, was evaluated in transient assays for GUS expression.

In carrying out the analysis, cavendish bananas were obtained from a local grocery store, and tested before ethylene treatment ("ungassed"), within 24 hours of a standard commercial ethylene treatment ("green, gassed") or approximately 2 to 3 days after ethylene treatment, when bananas had reached peel color index (PCI) 4 to 5 (mostly yellow peel, "half-ripe").

Gold particle suspensions of each construct were prepared and used to bombard sterilized ungassed green banana fruit, gassed banana fruit just before softening stage (not quite yellow) and gassed banana fruit 24 hours after gassing with ethylene, as detailed below in Examples 1 and 2. FIG. 7 illustrates the results of GUS reporter assays with the pAG142a-pel::GUS (PEL 2.0), pAG142b-pel::GUS (PEL 1.4), pAG142c-pel::GUS (PEL 0.9), pAG153-CsVMV::GUS (CsVMV), and pAG159-TRX::GUS (TRX 1.0) promoters in edible banana pulp (external surface of the pulp in contact with the peel) at green, peel color index (PCI) 1 (early) and PCI 4 (later) stages of ripening. The results are reported as the percent of banana fruit slices with GUS foci.

Melon Actin Promoter and Melon Actin/TRX Fusion Promoters

The relative activity of the melon actin, TRX-intron and TRX-actin fusion promoters of the invention was evaluated in a transient assay system using a GUS (β-glucuronidase) reporter gene, as described above.

Particle bombardment of various tissues including banana embryonic suspension cells, banana fruit slices and several types of garlic and onion tissue was carried out using the melon actin and TRX fusion promoters. Several plasmid constructs containing the GUS gene under transcriptional control of different promoters were evaluated by particle bombardment including: pAG138m-RE4::GUS; pAG147-promoterless GUS (which contains the GUS gene without regulatory elements and serves as a negative control); pAG153-CsVMV::GUS (which contains the CsVMV promoter and serves as a positive control); pAG167-mACTIN::GUS; PBI221-35S::GUS 9 (which contains the CaMV promoter and serves as a positive control); pAG749, TRX-actin; and pAG759, TRX-O2intron, as further described in Examples 3 and 4.

After bombardment and incubation in dark, samples were treated with X-gluc solution at 37° C. for 18 hours. Blue GUS foci were scored using an inverted microscope.

The melon actin promoter was evaluated together with various control promoters in both garlic and onion and the negative control (promoterless GUS) showed no foci, whereas the pAG138m-RE4::GUS; pAG153-CsVMV::pAG167-mACTIN::GUS; and PBI221-35S::GUS (CaMV 35S) all promoted GUS expression, as detailed in Example 3.

Particle bombardment of banana fruit slices was carried out using the modified TRX promoters. The GUS expression results indicate that the TRX-intron and TRX-actin modifications resulted in improved performance relative to the banana fruit-specific TRX promoter. More specifically, the TRX-actin fusion promoter displays transient expression activity approximately equal to the strong constitutive promoter CsVMV, whereas the TRX-intron promoter is slightly less active on average. Furthermore, the TRX-intron and TRX-actin promoters have lower activity in banana leaves, indicating that the promoters have retained the tissue specificity of the TRX promoter (Example 4).

Stable Transformation of Arabidopsis

The mACTIN promoter was also tested for activity in a model dicot (*Arabidopsis thaliana*) after transformation with a nucleic acid construct containing the reporter gene encoding GUS under the control of the mACTIN promoter. Plasmid pAG4015, which contains two expression cassettes: (1) adjacent to the left T-DNA border is found the selection cassette containing the nptII gene conferring kanamycin resistance under the control of the CsVMV promoter together with the G7 terminator; and (2) adjacent to the right T-DNA border is found the GUS reporter gene under the control of the mACTIN promoter together with the nos terminator.

*Arabidopsis thaliana* plants were transformed with pAG4015 by in planta Agrobacterium-mediated transformation, T1 seed was harvested from the plants, germinated and transformed seedlings identified based on kanamycin resistance, as further described in Example 3.

Histochemical staining for GUS activity indicated that the mACTIN promoter directs strong reporter gene expression in leaves, roots, stems and flowers (Example 3).

B. Methods of Detecting Promoter-Driven Gene Expression

Transgenic plants may be assayed for their ability to synthesize product mRNA, DNA, protein, and/or for their resistance to an antibiotic, e.g., the aminoglycoside antibiotic, kanamycin. The assays are typically conducted using various plant tissue sources, e.g., leaves, stem, or fruit Gene amplification and/or expression may be measured in a sample directly, for example, by conventional Southern blotting, Northern blotting to quantitate the transcription of mRNA [Thomas, 1980], dot blotting (DNA analysis), or in situ hybridization, using an appropriately labeled probe, based on the sequence or the transgene being expressed under the control of the various promoters described herein.

IX. Utility

The uses and benefits of the banana fruit-specific promoters described herein include the fruit specific expression of genes that may alter or improve characteristics of the fruit. Of particular interest are ripening control, modification of the nutritional content of fruit, and expression of useful proteins in a fruit-specific manner.

The melon actin promoter described herein is useful for controlling expression of selectable markers and for constitutive expression of genes of interest. It functions in both monocots and dicots and has activity similar to a commonly used viral promoter, but it is of plant origin.

The melon-actin fusion promoters described herein have similar properties, however, in addition they have retained the tissue specificity of the banana TRX promoter.

The following examples illustrate, but are in no way intended to limit the scope of the present invention.

Materials and Methods

DNA Plasmids and Agrobacterium Binary Vector Construction

Biological reagents were typically obtained from the following vendors: 5' to 3' Prime, Boulder, Colo.; New England Biolabs, Beverly, Mass.; Gibco/BRL, Gaithersburg, Md.; Promega, Madison, Wis.; Clontech, Palo Alto, Calif.; and Operon, Alameda, Calif.

Specific reagents employed in the particle bombardment include BioRad Biolistic PDS-1000/He system (BioRad Laboratories, Hercules, Calif., USA), gold particles of 1.5–3.0 μm (Aldrich, Milwaukee, Wis., USA), a rupture disk: 1,100 PSI (BioRad Laboratories, Hercules, Calif., USA), stop screens of 0.685 mesh (Rumsey-Loomis, Freeville, N.Y.), macrocarriers: (Rumsey-Loomis, Freeville, N.Y.) and X-Gluc: 5-Bromo-4-chloro-3-indoyl β-D-glucuronide cyclohexylamine salt (Rose Scientific, Edmonton, Alberta, Canada).

Standard recombinant DNA techniques were employed in all constructions (Adams and Yang, 1977; Ausubel, et al., 1992; Hooykaas and Schilperoot 1985; Sambrook, et al., 1989; and Maniatis, et al., 1989, all of which are expressly incorporated by reference, herein).

GUS Reporter Assays

Specific equipment and reagents employed in particle bombardment include BioRad Biolistic PDS-1000/He system (BioRad Laboratories, Hercules, Calif., USA), gold particles of 1.5–3.0 μm (Aldrich, Milwaukee, Wis., USA), a rupture disk: 1,100 PSI (BioRad Laboratories, Hercules, Calif., USA), stop screens of 0.685 mesh (Rumsey-Loomis, Freeville, N.Y.), macrocarriers: (Rumsey-Loomis, Freeville, N.Y.) and X-Gluc: 5-Bromo-4-chloro-3-indoyl β-D-glucuronide cyclohexylamine salt (Rose Scientific, Edmonton, Alberta, Canada).

Solutions for use in GUS assays included: 50% Glycerol (vol/vol); 2.5 M calcium chloride ($CaCl_2$, 13.875 grams anhydrous $CaCl_2$ dissolved in 50 mls sterile $diH_2O$); 0.1M spermidine (0.1452 grams dissolved in 10 mls sterile $diH_2O$); 70% EtOH (vol/vol), 3 mls sterile $diH_2O$ in 7 mls 200 proof ethyl alcohol; X-gluc solution (200 ml prepared by adding the components in the amounts shown in Table 1, below, to 198 ml distilled H$_2$O, stirring for 10 minutes or until dissolved, adjusting the pH to 7.0, dissolving 100 mg X-gluc in 2 ml DMSO, adding X-gluc/DMSO solution to the pH 7.0 solution, rinsing the X-gluc vial twice using the pH 7.0 solution, and filter sterilizing the resultant solution).

TABLE 1

Solutions for GUS Assay.

| Component | Amount | Final Conc. |
|---|---|---|
| EDTA, Disodium salt | 0.744 g | 10.0 nM |
| NaH$_2$PO4.H$_2$O monobasic, monohydrate | 1.760 g | 100.0 mM |
| K$_4$Fe(CN)$_6$.3H$_2$O | 0.042 g | 0.5 mM |
| Triton X-100 | 0.200 ml | 0.1% |

Gold particle suspensions are prepared by adding 30 µl of gold particles (1.5 µm to 3.0 µm) to a high quality microcentrifuge tube followed by addition of 1 ml 70% EtOH. The suspension is vortexed for 20 seconds and left to stand for 25 minutes, allowing the particles to settle to the bottom of the tube so that they do not stick to the side of the tube when centrifuging, followed by centrifuging in a microcentrifuge for 6 minutes at 13,000 rpm. The supernatant is carefully removed, discarded and 500 µl sterile diH$_2$O added to the tube which is vortexed for 10 seconds and left standing for 25 additional minutes, followed by centrifuging in a microcentrifuge for 6 minutes at 13,000 rpm. The supernatant is carefully removed, discarded, 500 µl sterile 50% glycerol stock added and the mixture vortexed until the particles are resuspended.

DNA solutions containing the GUS recombinant nucleic acid constructs were prepared by adding 50 µl (1 µg/µl) DNA to a microcentrifuge tube containing the gold and gently vortexing for 2–3 seconds, followed by adding 500 µl cold CaCl$_2$ (2.5M) and gently vortexing for 2–3 seconds, adding 200 µl cold spermidine (0.1M) and gently vortexing at low speed at 4° C., tapping the tube a couple of times every 5–10 minutes to make sure particles remained suspended, with a total vortex time of about 40 minutes. The centrifuge tube was pulsed to a maximum of 1,500 rpm in a microcentrifuge at 4° C. three times, the supernatant removed and discarded. 1 ml cold 70% was then added, the solution mixed and the pulse centrifuge step repeated with the supernatant removed and discarded. This pulse centrifuge step was repeated using cold 100% EtOH, followed by adding 350 µl cold 100% EtOH and resuspending the particles by gently vortexing for 2 seconds.

Banana fruit was prepared for particle bombardment by wiping with a towel soaked in 95% ethyl alcohol, trimming off the pedicel stalk and the tip of the fruit, and placing in a beaker. An amount of a water/soap mix (4 drops antimicrobial soap/1000 ml H$_2$O) sufficient to cover the fruit was added and shaken intermittently for 15 minutes, then rinsed with diH$_2$O, until the soap was gone. An amount of 75% EtOH sufficient to cover the fruit was added and shaken gently each minute for 4 minutes, the EtOH was drained off and an amount of 10% bleach/2 drops Tween 20/1000 ml sufficient to cover the fruit was added and shaken intermittently for 10 minutes. The bleach was drained off and the fruit rinsed 3 times with sterile diH$_2$O, followed by rinsing once with sterile 500 ml diH$_2$O/2 ml PPM mix (Plant Preservative Mixture, Plant Cell Technology, Washington, D.C.), and soaking in media consisting filter sterilized 200 mg/l ascorbic acid and 200 mg/l citric acid, until ready to be cut. Before cutting, the fruit was blotted dry on filter paper.

Ungassed green banana fruit, gassed banana fruit just before softening stage (not quite yellow) and gassed banana fruit 24 hours after gassing were generally used in transient assays. The types of tissue used included, longitudinal slices of the outside of the fruit pulp without peel (the portion that touches peel), segments of the inside of the peel, segments of the outside of the peel, cross sectional slices including the peel and longitudinal slices of the seed region (middle portion of the fruit).

After cutting, the fruit was plated onto PAC1 medium, which contains: MS salts, B5 vitamins, glycine 2 mg/l, sucrose 3%, casein hydrolysate 100 mg/l, BA 0.5 mg/l, 2,4-D 1.5 mg/l, PPM 5 ml/l, ascorbic acid 100 mg/l, citric acid 100 mg/l, cefotaxime 200 mg/l (aa) pH 5.8 and Phytagel 0.25.

The transient assay is based on particle bombardment of plant tissue sections with a suspension of DNA and gold particles as described above. The fruit tissue was bombarded using GUS reporter constructs, a flight distance of 6 cm and a PSI of 1,100. Flight distance is defined as the distance between the DNA coated microcarrier and stopping screen to the target cells. PSI refers to the helium pressure in the gas acceleration tube used for particle bombardment. After the fruit tissue was bombarded, it was sealed with parafilm and left in the dark at 24° C. for 22 hours, then explants were carefully transferred to clean, sterile petri plates and X-gluc solution added to completely cover the fruit. Plates were stored in an incubator at 37° C. for 18 hours, then the X-gluc solution was drained off and 95% EtOH added to cover the fruit. Observations were made using a microscope and counting the number of GUS foci on each slice of fruit.

EXAMPLE 1

Use of Differential Display to Identify Banana-Specific Transcripts

Differential display was performed using total banana RNA from pulp (PCI 4, yellow ripe), root, corm, and leaf from greenhouse-grown plants, and in vitro plantlets (root and shoot), using the GenHunter RNAImage Kit Number 1, according to the supplier's protocol. RNAimage® Kits [Cat. No.: G501-G510], GenHunter Corporation, 624 Grassmere Park Drive, Suite 17/Nashville, Tenn. 37211/USA, Tel: 615-833-0665/Fax: 615-832-9461, genhunt@telalink.net http://www.nashville.net/genhunt/kimage . html].

First-strand cDNA was synthesized from 50 µg DNase-treated total RNA using single-base anchored oligo(dT) primers containing a HindIII restriction site (H-T$_{11}$G, SEQ ID NO:15; H-T$_{11}$A, SEQ ID NO:16; and H-T$_{11}$C, SEQ ID NO:17). The cDNA was then amplified in duplicate in the presence of a radiolabeled nucleotide (in this case, γ-[33P] dATP), and the resulting products analyzed on a denaturing polyacrylamide gel. Products specific to a certain tissue were identified after separation and autoradiography. After desired amplification products were identified, they were recovered directly from the dried acrylamide gel, re-amplified with the original primer set, then further characterized.

When the G-anchored primer (H-T$_{11}$G, SEQ ID NO:15) was used for the amplifications, along with arbitrary primers, H-AP1 through H-AP8 (SEQ ID NOs:7–14; GenHunter Corp., Nashville, Tenn.), several amplified differential display products were found to be unique to pulp and undetectable in root, corm, leaf, or in vitro plantlet tissue. Among these were an approximately 400 bp product using the AP1 primer(G1A, SEQ ID NO:22, GenHunter Corp., Nashville, Tenn.).

Isolation of a Banana Fruit-Associated G1a (TRX) Promoter

Amplification products associated with ripe banana pulp were recovered from acrylamide gels, re-amplified with the original primer set, and the differential display products used as probes on Northern blots to confirm tissue distribution of the associated transcript. Results from Northern blot analysis using G1A (TRX) as a probe indicate that the native transcript is approximately 600 nucleotides long and highly fruit-associated.

Upstream sequences associated with the banana differential display product TRX, were isolated in a series of steps. The first oligonucleotide primer was designed complementary to the 5' end of the differential display fragment and used to walk upstream in a PCR-accessible banana genomic library (Universal Genome Walker Kit, catalog #K1807, Clontech Laboratories, Inc., 1020 East Meadow Circle, Palo Alto, Calif. 94303–4230). PCR-accessible banana genomic libraries were constructed and screened according to the supplier's protocol, using the five restriction endonucleases included in the kit (EcoRV, Sca I, Dra I, Pvu II, and Ssp I), and three additional blunt-cutters which were used to digest genomic DNA prior to adaptor ligation: HpaI, MscI, and PshAI. After two rounds of amplification of the banana libraries using thrdx 3'R (SEQ ID NO:18) and H-AP1 (SEQ ID NO:7, GenHunter Corp., Nashville, Tenn.) primers in the primary reaction and primers thrdx3'R (SEQ ID NO:18) and H-AP2 (SEQ ID NO:8, GenHunter Corp., Nashville, Tenn.) in the secondary reaction, a 600 bp (#13) and a 620 bp (#14) fragment were amplified from the DraI library.

The fragments each consisted of a partial intron I, followed by exon II and intron II and a partial exon III. The nucleotide sequence of exon II and the partial exon III was identical between fragments #13 and #14. However, sequence differences in the introns were apparent. In fragment #13, the predicted intron II size is 90 bp, while the predicted intron size in fragment #14 is 96 bp, due to a 6 nucleotide insertion. Two nested oligonucleotide primers complementary to the exact sequence of the fragment #14 intron I were designed; trx 3'R-2 (SEQ ID NO:19) and trx 3'R-3 (SEQ ID NO:20), which contains a single base mismatch between the primer sequence and the sequence of fragment #13.

Using these two gene-specific primers to walk upstream in the banana PCR-accessible libraries, a 1.2 kb fragment was amplified from the PshAI library. The fragment contained the rest of intron I, the complete exon I, and upstream sequence, including a putative TATA-box. The nucleotide sequence of this 1.2 kb fragment was identical to the intron I sequence of fragment #14 described previously.

A 5'RACE product was amplified from a PCR-accessible cDNA library made from banana pulp (PCI 4) RNA (Marathon cDNA Amplification Kit, Clontech) using the thrdx3'R primer (SEQ ID NO:18). The 300 bp product matched the sequence of the exons in the 1.2 kb fragment, which in turn was contiguous with fragment #14.

Several gene specific oligonucleotide primers were designed and used in PCR amplifications to verify that the 1.2 kb fragment and fragment #14 were contiguous with the genomic fragments encoding the 5'RACE fragment and the differential display product G1A and that the contiguous DNA fragment was unique in the banana genome (i.e., representing a single gene).

Single products were obtained after RT-PCR and amplification of genomic DNA with gene-specific primers, and the identity of the products was further verified by restriction digests.

An additional upstream walk was performed, using the TRX14A (SEQ ID NO: 23), and TRX14B (SEQ ID NO:24), primers designed from the sequence of the 1.2 kb fragment contiguous with the original fragment #14, and an 800 bp fragment was obtained.

The entire nucleotide sequence of the banana TRX gene is shown in FIG. 1 (SEQ ID NO:1), which depicts the complete annotated nucleotide sequence, including the coding sequence and intron(s). Nucleotides 13 through 990 of SEQ ID NO:1 correspond to the banana fruit-associated TRX promoter of the invention, presented herein as SEQ ID NO:2.

Restriction sites were engineered into the primers used to amplify the TRX promoter directly from banana genomic DNA in order to clone the sequence. A BamHI site and NcoI site were engineered into the 5' and 3' primers, TRXP-F (SEQ ID NO:25) and TRXP-R (SEQ ID NO:26), respectively, in order to incorporate cloning sites for use in preparation of recombinant nucleic acid constructs, as further described below.

Plant Transformation Vectors and Banana TRX Promoter Activity Using Reporter Constructs Restriction sites were engineered into the primers used to amplify the TRX promoter directly from banana genomic DNA, for ease of cloning. A BamHI site and NcoI site were engineered into the 5' and 3' primers, TRXP-F (SEQ ID NO:25) and TRXP-R (SEQ ID NO:26), respectively. The TRX promoter was amplified from banana genomic DNA, digested to produce the appropriate cohesive ends, and cloned into compatible sites in a reporter gene construct, comprised of the promoter translationally fused with GUS (β-glucuronidase) and containing the nos terminator. The resulting construct was named pAG159. The nucleotide sequence of the TRX promoter, as it exists in pAG159, is presented in SEQ ID NO:2 (FIG. 2). The TRX promoter sequence in pAG 159 (FIG. 2) differs from the nucleotide sequence assembled from genomic amplifications (FIG. 1) in that a BamHI site (GGATCC) and an NcoI site (CCATGG) have been engineered into the 3' and 5' ends of the sequence, respectively. The translational start codon consists of the ATG contained within the 3' NcoI site. The sequence in FIG. 2 (SEQ ID NO:2) has been shown to encode a functional promoter.

pAG159-TRX::GUS, pAG142a-pel::GUS (2.0 kb), pAG142b-pel::GUS (1.4 kb), pAG142c-pel::GUS (0.9 kb), pAG153-CsVMV::GUS and pBI221-35S::GUS recombinant nucleic acid constructs were individually introduced into banana tissue by particle bombardment.

The pBI221-35S::GUS and pAG153-CsVMV:GUS constructs contain the CaMV 35S and CsVMV promoters, respectively, which drive GUS expression. Both are strong constitutive promoters which serve as positive controls for expression.

The relative activity of the banana fruit-associated promoters was determined by transient assay system using the GUS reporter gene.

The transient assay is based on particle bombardment of plant tissue sections with a suspension of DNA and gold particles as described above.

After the fruit tissue was bombarded, it was sealed with parafilm and left in the dark at 24° C. for 22 hours, then explants were carefully transferred to clean, sterile petri plates and X-gluc solution added to completely cover the fruit. Plates were stored in an incubator at 37° C. for 18 hours, the X-gluc solution drained off and 95% EtOH added to cover the fruit. Observations were made using a microscope and counting the number of GUS foci on each slice of fruit. FIG. 7 illustrates the results of GUS reporter assays, presented as the percent of banana fruit slices with GUS foci.

EXAMPLE 2
Isolation of a Banana Fruit-Associated PEL Promoter

A cDNA library was generated using RNA isolated from ripening banana pulp. Total banana RNA was extracted from banana pulp tissue (PCI 4) using the protocol in Clendennen and May, 1997, and poly(A)+ RNA was isolated from 17 µg DNase-treated total RNA using the Straight A's mRNA Isolation System Kit [Novagen, Inc., Madison, Wis.]. The library was made using Clontech's Marathon cDNA Amplification Kit [Clontech Laboratories, Inc.: Marathon cDNA Amplification Kit, Palo Alto, Calif. 94303-4230], following the manufacturer's protocol. Briefly, after first and second-strand cDNA synthesis, adaptors were ligated to the polished ends of the double-stranded cDNA. This cDNA library served as a PCR-accessible library for rapid amplification of cDNA 5' or 3' ends.

A rapid amplification of cDNA 5' ends (5' RACE) reaction was performed with adaptor-specific and PEL1 gene-specific (PEL 3'R-2, SEQ ID NO:27) oligonucleotide primers. The 5' end of the banana PEL1 cDNA was amplified using the manufacturer's suggested conditions for RACE amplifications (Clontech). A 5' RACE product of approximately 900 bp was isolated, cloned, and sequenced. A putative translational start site was identified and gene-specific oligonucleotides were designed to walk upstream in a banana genomic library.

The pectate lyase (PEL) fruit-associated promoter was isolated in a series of steps. A PCR-accessible genomic library was made from banana genomic DNA using the Clontech Universal GenomeWalker Kit [Clontech Laboratories, Inc, Palo Alto, Calif.]. Following the suggested protocol from the manufacturer, five blunt-cutter restriction enzymes were used separately to digest genomic banana DNA: DraI, EcoRV, PvuII, ScaI, and StuI. Once purified, the digested DNA fragments were ligated to adaptor ends supplied in the kit. This served as a PCR-accessible library for amplification of genomic sequence upstream of the PEL1 start codon.

Two gene-specific oligonucleotides (PFBAN3'R, SEQ ID NO:28, and PF Pec 3'R, SEQ ID NO:29), were used in nested primer reactions, and a putative promoter fragment of approximately 2.5 kb was amplified from the ScaI digested genomic banana library. The fragment was cloned and completely sequenced.

The PEL1 2.5 kb promoter fragment was subcloned as a translational fusion with GUS in a reporter gene construct. It was engineered with a 5' end PstI site and 3' end SnaBI site. In addition to assaying promoter function of the 2.5 kb PEL1 promoter fragment, a series of 5' deletions was generated from the 2.5 kb PEL1 upstream sequence. The PEL1 deletions were made by restricting the cloned fragment with SphI and SpeI restriction enzymes, leaving intact a 5' overhang susceptible to enzymatic digestion by $E.\ coli$ exonuclease III [New England Biolabs, Beverly, Mass.]. Following a published protocol provided in New England BioLab's Exo-Size Deletion Kit, [New England Biolabs, Beverly, Mass.], the digestion was stopped at 20 second intervals by removing 2 µl of the DNA/$E.\ coli$ exonuclease mix at 37° C. Aliquots were transferred to tubes containing mung bean nuclease [New England Biolabs, Beverly, Mass.], and incubated at 37° C. for 15 minutes. Any residual overhangs were removed by digestion with mung bean nuclease leaving blunt ends. The truncated fragment was then self ligated with T4 DNA ligase to regenerate a circular plasmid. Truncated PEL1 promoter fragments of 2.0, 1.4, and 0.9 kb in a translational fusion with GUS were generated by this method. The complete nucleotide sequence of the 2.0 kb PEL promoter, as it exists in the GUS reporter construct pAG142a, is shown in FIGS. 5A and B. The 5' end of the 1.4 and 0.9 kb truncations is also indicated in the figure. The sequence of the PEL 2.0 kb promoter is presented in FIGS. 3A and B and as SEQ ID NO:3. The PEL 1.4 kb and 0.9 kb promoters, correspond to nucleotides 564 to 2010 and 1099 to 2010, respectively, of the PEL 2.0 kb promoter sequence presented as SEQ ID NO:3.

Plant Transformation Vectors and Banana PEL Promoter Activity Using Reporter Constructs The 2.5 kb PEL1 promoter fragment, described above was generated, truncated as PEL1 promoter fragments of 2.0, 1.4, and 0.9 kb, digested to produce the appropriate cohesive ends, and cloned into compatible sites in a reporter gene construct, comprised of the promoter translationally fused with GUS (β-glucuronidase) and containing the nos terminator. The resulting constructs comprising PEL1 promoter fragments of 2.0, 1.4, and 0.9 kb were named pAG142a-pel::GUS (2.0 kb), pAG142b-pel::GUS (1.4 kb) and pAG142c-pel::GUS (0.9 kb), respectively. The PEL1 fragments (2.0, 1.4 and 0.9 kb) correspond to nucleotides 1 to 2010, 564 to 2010 and 1099 to 2010, respectively, of SEQ ID NO:3.

Banana fruit was prepared for particle bombardment as described above. The pAG142-pel::GUS (2.5 kb); pAG142a-pel::GUS (2.0 kb), pAG142b-pel::GUS (1.4 kb), pAG142c-pel::GUS (0.9 kb), pAG153-CsVMV::GUS, pAG159-TRX::GUS and pBI221-35S::GUS recombinant nucleic acid constructs were individually introduced into banana tissue by particle bombardment. The relative activity of the banana fruit-associated promoter in the various constructs was determined by transient assay based on GUS reporter expression. FIG. 7 illustrates the results of GUS reporter assays, presented as the percent of banana fruit slices with GUS foci.

EXAMPLE 3
Isolation and Characterization of a Melon Actin Promoter

Several plant actin nucleotide sequences from GenBank including those found at GenBank Accession Numbers: D88414, cotton; D78206, morning glory; AB002819, mint; X67666, pea; U60483, potato; U60496, soybean; U60489, tobacco and U60478, tomato were selected, aligned using the Clustal-W program with default parameters, and conserved regions within the coding sequence identified. Oligonucleotide primers were synthesized complimentary to the conserved regions and used to amplify actin fragments both from plant cDNA and genomic DNA (genDNA) templates. The primers, ACTIN 5'F (SEQ ID NO:30) and ACTIN 3'R (SEQ ID NO:31) span intron 3, which occurs at the 5' end of the resulting PCR product and have been effective amplify genDNA and cDNA templates from many different monocots and dicots, including apple, banana, cherry, grape, lettuce, maize, melon, pea, raspberry, tobacco, and tomato.

In melon, the genomic PCR fragment was slightly larger than the corresponding RT-PCR product, consistent with the presence of a small intron in the genomic fragment. The melon genomic and RT-PCR fragments were sequenced and it was determined that the sequences were identical except for the presence of a single intron, corresponding to an intron formerly designated "intron 3". In melon the intron is 87 nt long and is not conserved between melon and other plant species.

Using both the coding and intron sequences, complimentary nested oligonucleotide primers were synthesized that amplify a fragment upstream of the melon actin coding sequence. The primers amplified a 1.6 kb fragment from the melon DraI promoter finder library. The fragment was cloned and sequenced. The melon actin genomic fragment contains approximately 540 bp of 5' flanking sequence upstream of the translational start site and 1 kb of transcribed sequence, which contains exons 1, 2, and a small portion of 3, and introns 1 and 2. The transcriptional start site was estimated by amplifying and sequencing a 5' RACE fragment of the actin transcript from melon cDNA. Upstream elements with homology to functional motifs characterized in other plant actin promoters have also been identified.

Oligonucleotide primers used to amplify a melon actin gene fragment containing upstream regulatory regions included PF1 (SEQ ID NO:32), PF2 (SEQ ID NO:33), Actin PFb (SEQ ID NO:34), Actin PFc (SEQ ID NO:35) and MACTP int1 (SEQ ID NO:36).

The complete nucleotide sequence of the melon actin promoter, up to and including the translational start site, is presented in FIG. 4. The transcriptional start site, as estimated by characterization of 5'RACE products, is indicated as +1 in the sequence, placing the putative TATA-box at −47. Features indicated as underlined in FIG. 4 include the putative TATA-box at −47, nucleotides −251 to −205 in the melon actin promoter which is an A-rich region similar to the poly(dA-dT) region identified between nt positions −190 and −140 in the rice actin promoter. The rice actin poly(dA-dT) was shown to act as a strong positive regulatory region for constitutive expression (Wang et al., 1992). Nucleotides −185 to −146 constitute a region similar to the region between −150 and the TATA-box in the Arabidopsis ACT2 and ACT8 5' flanking sequences (An et al., 1996). This region is highly conserved between the two Arabidopsis actin gene family members and may indicate the position of functional elements. The underlined region from nucleotides −119 to −96 indicates a short direct repeat [4X(GCATTT)], a sequence motif that is present within an ORF of *Sacchromyces cerevisiae* and in non-coding regions of the *Drosophila melanogaster* and *Arabidopsis thaliana* genomes. Motif (−84 to −51) is a region containing a dinucleotide repeat [18X(CT)] which motif is also present in the soybean Ac7 gene 5' flanking region. The (−119 to −96) and (−84 to −51) repeats are of unknown function.

The melon actin promoter sequence exhibits similarities to both the rice (model monocot) and Arabidopsis (model dicot) strong constitutive actin promoters, and also to the soybean Ac7 actin gene 5' flanking sequence. The melon actin promoter does not contain the putative root-associated expression element (CCCAA repeat) present in the rice actin promoter, and also contains unique sequence motifs. The similarities at the nucleotide sequence level are summarized in Table 2, which presents the distribution of sequence motifs in the constitutive rice (monocot), Arabidopsis and soybean (dicot) actin promoters compared to the melon actin promoter. The approximate position of the sequence motif, if present, is indicated relative to the transcriptional start site.

TABLE 2

Actin Promoter Sequence Motifs.

| Motif | mACTIN | Soybean Ac7 | Arabidopsis ACT2/8 | Rice Act1 |
|---|---|---|---|---|
| [CCCAA]X7 | not present | not present | not present | −300 |
| poly(dA-dT) | −250 | −240 | −230 (ACT8 only) | −190 |
| At −150 | −190 | −190 | −150 | not present |
| [GCATTT]X4 | −120 | not present | not present | not present |
| [CT]X18 | −90 | −160 | not present | not present |
| size of 5' intron | 838 nt | 844 nt | 442 nt/461 nt | 447 nt |

Promoter Activity of mACTIN

The melon actin fragment amplified from genomic DNA up to the translational start site ("mACTIN") was subcloned to test its ability to promote expression of operably linked heterologous genes. Construct pAG167 contains the full-length (1.5 kb) melon actin upstream genomic fragment cloned as a translational fusion with the uidA reporter gene encoding GUS. The pAG167 GUS reporter gene construct is contained in a pUC vector. The construct pAG4015 contains the full-length melon actin promoter operably linked (as a translational fusion) with the reporter gene encoding GUS, along with a selection cassette composed of the CsVMV promoter which controls expression of the nptII gene and confers kanamycin resistance. This construct is contained within the pPZP2000 binary vector.

Plant Transformation Vectors and Melon Actin Promoter Activity Using Reporter Constructs Banana The promoter activity of mACTIN was tested in banana embryogenic suspension cells using the construct designated "pAG167" (mACTIN-GUS). Assays were performed at the Boyce Thompson Institute for Plant Research BTI (Ithaca, N.Y.), where pAG167 was used to bombard embryogenic suspension cells of banana and relative GUS activity measured in protein extracts from the bombarded tissue as described below. The results of these assays indicated that level of GUS by pAG167 was comparable to that of the CaMV35S control.

Two 7-day old GN embryogenic suspension cells (*Musa acuminata* cv Grand Nain; ES23 and ES35) were provided by Nicole Higgs. Cell suspensions were pooled and filtered through a coarse sieve and diluted to a packed cell volume:liquid volume of approximately 1:6. A 400 µl volume of resuspended cells was dispersed onto Whatman filter disks on solid media and stored for two days under standard growth conditions (total: 66 plates). Test plasmids used for bombardment included pAG167 (mACTIN-GUS) and control plasmids included pCaMV35S-GUS and pmaizeUbi-GUS, containing the uidA gene encoding GUS under the transcriptional control of the cauliflower mosaic virus 35S promoter and the maize ubiquitin promoter, respectively. For the bombardments, gold particles were coated with 2 µg of QIAGEN pure plasmid DNA of each test construct. Six plates of GN cells were bombarded (10 µl Au:DNA mix, 800 psi) per construct. Six GN plates were kept aside as unbombarded negative controls. Two days post-bombardment, one plate per construct was histochemically assayed for GUS activity (X-gluc). Three days post bombardment, total protein was extracted from the remaining 5 plates per construct (total: 55 plates). Protein concentration was estimated for each extract using the Bradford assay and 50 µg of total protein was used for GUS fluorometric assays (4-MU) allowing direct quantitative comparisons of promoter activity. Fluorescence was measured using a Dynex Technologies Fluorolite 1000 (Ref value 3: 1770, lamp voltage 6.9). The results are shown in Table 3 as the average fluorescent signal units and the standard deviation. The results of GUS staining correlated well with the fluorometric assays, i.e., only pAG167 demonstrated significant GUS expression in comparison to the ubi and CaMV35S controls.

TABLE 3

GUS Activity In Banana Embryogenic Suspension Cells.

| Construct | Fluorescence signal (standard deviation) |
| --- | --- |
| negative control (no construct) | 279.2 (25.9) |
| pmaizeUbi-GUS | 20715.2 (11440.6) |
| pCaMV35S-GUS (pBI221) | 8266.4 (3789.1) |
| mACTIN-GUS (pAG167) | 7189.6 (1750.1) |

Allium Methods and Results

In addition, the mACTIN promoter was assayed for promoter activity in Allium spp. (garlic, *Allium sativum* and onion, *Allium cepa*). Bombardment of onion and garlic target tissues with various reporter constructs was followed by histochemical GUS staining.

Local market varieties of garlic and onion were used as target tissues for gene expression studies. In order to prepare tissues for particle bombardment, dry outer peels were removed from onion bulbs, and garlic cloves. They were surface sterilized by a modified sterilization protocol using ethanol and bleach, where the garlic or onion is peeled, wiped with a towel soaked in 95% ethyl alcohol, placed in a beaker to which is added an amount of a water/soap mixture sufficient to cover the samples, shaken intermittently for 10 minutes, then rinsed with $diH_2O$ until the soap is gone. 75% EtOH was then added to cover the garlic or onion sample which is shaken gently each minute for 4 minutes, the EtOH is then drained off followed by the addition of sufficient 10% bleach/2 drops Tween 20/1000 ml to cover the samples followed by intermittent shaking for 10 minutes. The bleach was then drained off, the samples rinsed 3 times with sterile $diH_2O$ and once with sterile 500 ml $diH_2O$/2 ml PPM mix (Plant Preservative Mixture, Plant Cell Technology, Washington, DC). The samples were cut and bombard on the same day.

The sterilization procedure specific to in vivo leaves of scallion included the steps of agitating the leaves gently in 70% EtOH for 30 seconds, draining off the EtOH, agitating the leaves gently in 10% bleach with Tween20 for 1 minute, draining off the bleach, rinsing 3 times with sterile water, and rinsing 1 time with 2 ml PPM in 500 ml sterile water. This was followed by cutting the leaves into segments and plating them abaxial side up (exterior side up) on PAC1 medium. The samples were cut and bombard on the same day.

After cutting, garlic or onion samples were plated onto PAC1 medium containing: MS salts, B5 vitamins, glycine 2 mg/l, sucrose 3%, casein hydrolysate 100 mg/l, BA 0.5 mg/l, 2,4-D 1.5 mg/l, PPM 5 ml/l, ascorbic acid 100 mg/l, citric acid 100 mg/l, cefotaxime 200 mg/l (aa) pH 5.8 and Phytagel 0.25.

The types of garlic tissue tested included: (1) the exterior of a garlic clove, cut in half longitudinally; (2) a cross sectional slice of clove; and (3) the interior of a garlic clove, cut in half longitudinally. 14–22 pieces of garlic were bombarded for each construct tested except pAG167 (mACTIN) for which only 6 pieces were bombarded.

The types of onion tissue tested included: (1) the exterior of the bulb rings from a large white onion; (2) the interior of the bulb rings from a large white onion; (3) a cross sectional slice of the bulb from a large white onion; (4) the exterior of the bulb from scallion, cut in half longitudinally; (5) the interior of the bulb from scallion, cut in half longitudinally; (6) a cross sectional slice of a scallion bulb; (7) adaxial leaf segments (interior) from scallion and (8) abaxial leaf segments (exterior) from scallion. 14–20 pieces of onion were bombarded for all constructs except pAG167 (mACTIN) for which only 4 pieces were bombarded.

Particle bombardment was carried out using a PDS 1000/He microprojectile gun (Bio-Rad) and gold particles, as described above for banana. Four different plasmid constructs containing the GUS gene under transcriptional control of various promoters were evaluated including: pAG138m-RE4::GUS, pAG147-promoterless GUS (which contains the GUS gene without regulatory elements, and serves as a negative control), pAG153-CsVMV::GUS (which contains the CsVMV promoter and serves as a positive control), pAG167-mACTIN::GUS and PBI221-35S::GUS (which contains the CaMV promoter and serves as a positive control). (See Example 3.)

After bombardment and incubation in dark, samples were treated with X-gluc solution at 37° C. for 18 hours. Blue GUS foci were scored using an inverted microscope. Summary results from the bombardment of garlic and onion tissues are presented in FIGS. 8A and B, respectively. Blue foci were observed in all the X-gluc treated tissues except in the negative control bombarded with promoter-less GUS. Blue foci could be easily scored on the exterior of garlic clove and onion bulb (onion rings). The problem of intrinsic blue previously described relative to Allium species (Barandiaran et al., 1998) did not pose a problem in our investigation. However the blue foci due to GUS expression were distinctly different from the surrounding blue shade, as can be seen in FIGS. 9A–D and FIGS. 10A–D for exemplary GUS assay results with control promoters in garlic and onion, respectively.

Figure 8A:
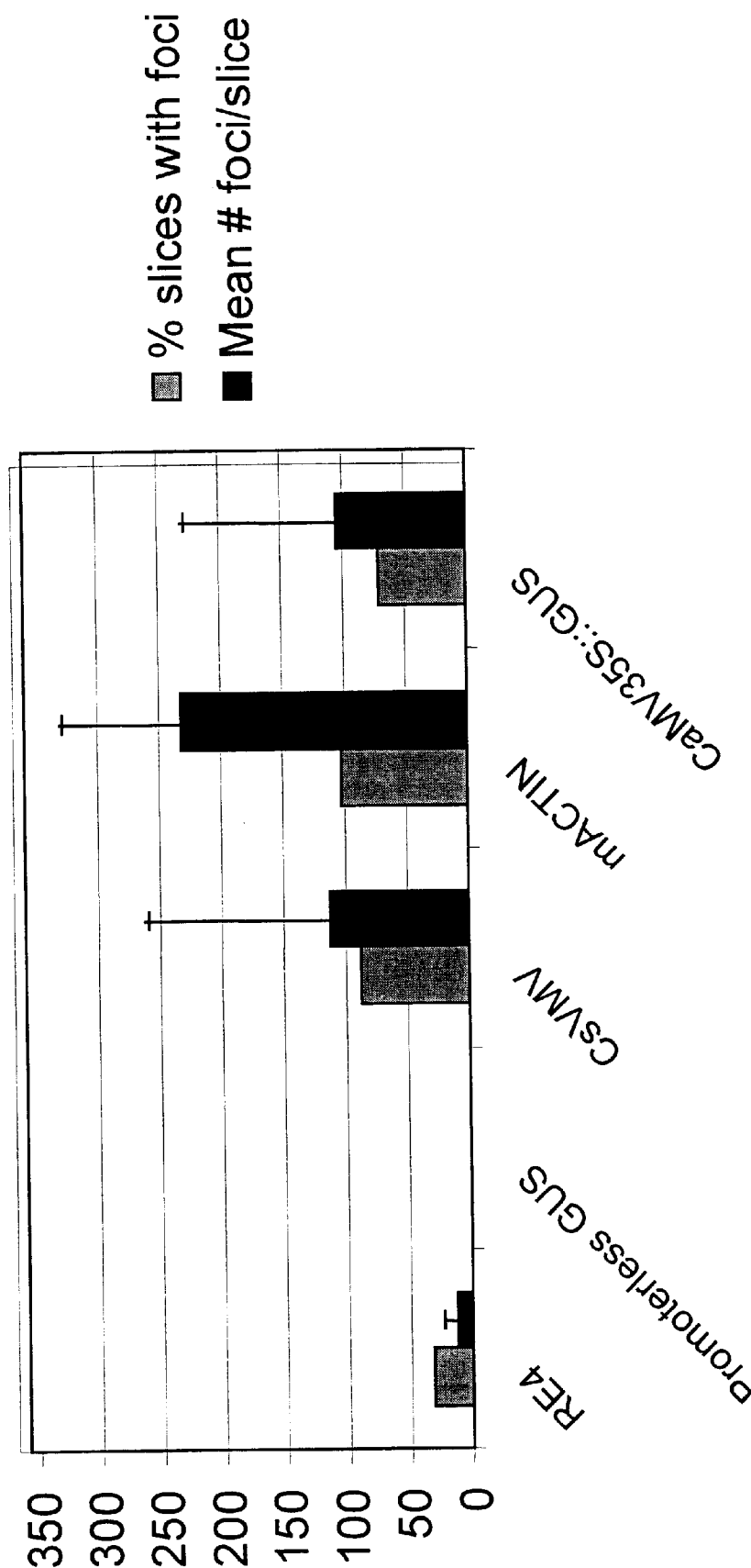
FIGS. 8A and 8B illustrate the relative promoter activity of GUS reporter constructs in garlic (exterior of clove, FIG. 8A) and onion (exterior of bulb, white onion; and onion leaves, scallion, FIG. 8B). RE4 promoter, promoterless GUS, CsVMV, mACTIN and CaMV 35S promoter constructs in translational fusion with the reporter gene GUS were introduced into garlic or onion tissue by microprojectile bombardment. The results are reported as % of slices with foci and as the mean number of foci per slice.

In garlic, the negative control (promoterless GUS) showed no foci, whereas all other promoters tested did (FIG. 8A). Tissue bombarded with a construct comprising GUS under the control of the mACTIN promoter showed the highest percentage of slices with GUS foci (100%). Tissue bombarded with a construct comprising GUS under the control of the CsVMV, CaMV35S and RE4 promoters showed 86%, 68%, and 31% of slices with foci, respectively.

Figure 8B:
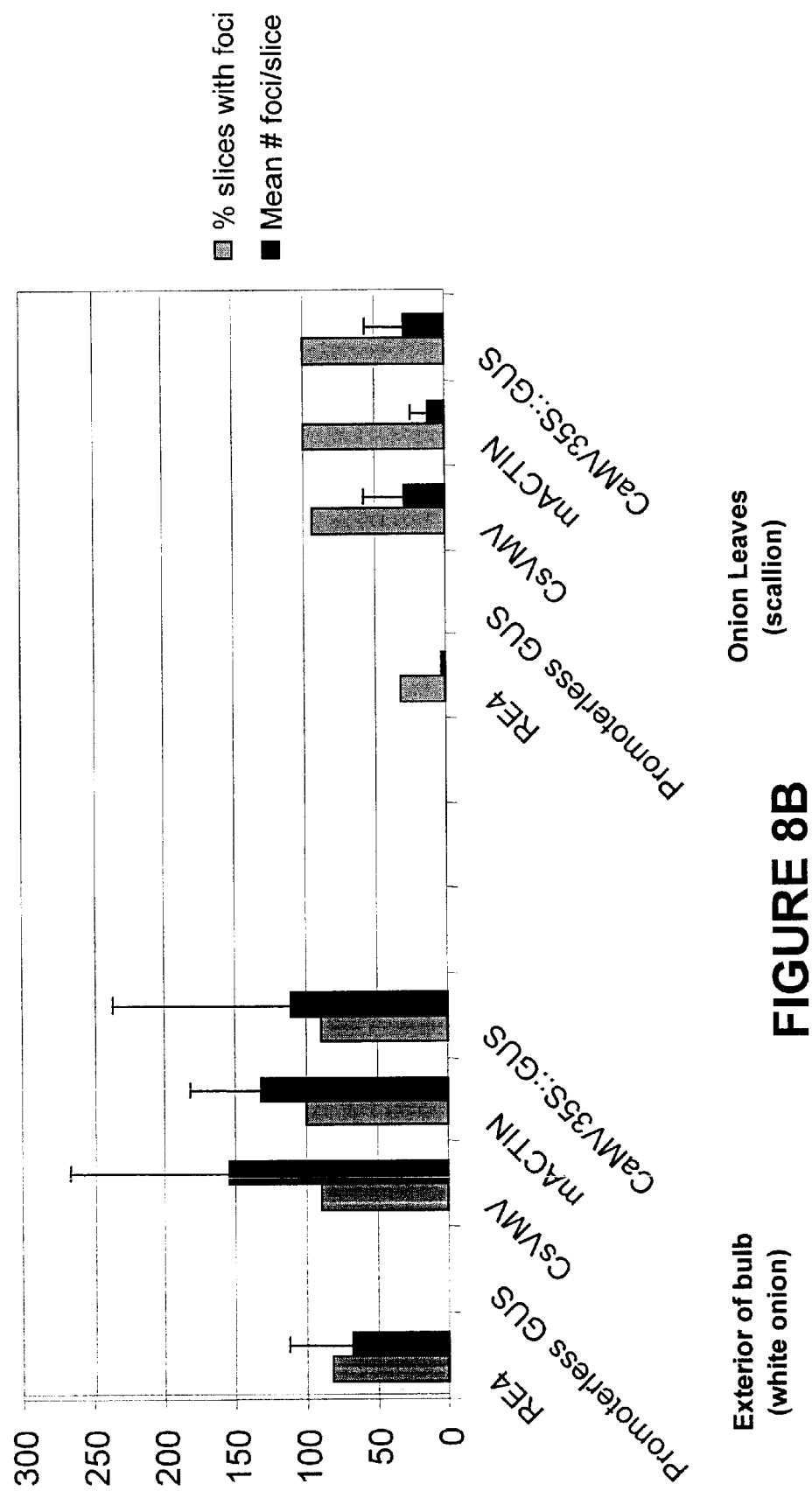

In onion, the negative control (promoterless GUS) showed no foci in onion bulbs or scallion leaves, whereas all other promoters tested did (FIG. 8B). Tissue bombarded with a construct comprising GUS under the control of the mACTIN promoter showed the highest percentage of slices with foci (100%), based on the number of samples tested. The positive control CaMV35S promoter showed 90% of slices with foci, followed by CsVMV with 88%, and RE4 with 81% of slices with foci.

Bombardment of leaf segments of scallion resulted in 100% of segments with GUS foci for both the mACTIN and CaMV35S promoters, 93% of segments with GUS foci for the CsVMV promoter and 31% of segments with GUS foci for the RE4 promoter (FIG. 8B).

In summary, pAG153 (CsVMV) and pAG167 (MACTIN) demonstrated stronger expression of GUS than the CaMV 35S promoter (pBI221) in garlic cloves and onion bulbs. In scallion leaves, GUS expression under the control of pAG153 (CsVMV) and pAG167 (mACTIN) was similar to that of the CaMV 35S promoter (pBI221).

Stable Transformation of Arabidopsis

The mACTIN promoter was also tested for activity in a model dicot (*Arabidopsis thaliana*) after transformation with a nucleic acid construct containing the reporter gene encoding GUS under the control of the mACTIN promoter. Construct pAG4015 contains two expression cassettes: adjacent to the left T-DNA border is found the selection cassette contains the nptII gene conferring kanamycin resistance under the control of the CsVMV promoter and the G7 terminator; and adjacent to the right T-DNA border is found the GUS reporter gene under the control of the mACTIN promoter and the nos terminator.

*Arabidopsis thaliana* (Col-0 ecotype) plants were grown in soil under long day conditions (16 h of light). The primary inflorescences were trimmed from the plants to encourage growth of lateral inflorescence, and plants were transformed 6 days after the trimming. The Agrobacterium strain GV3101 containing helper plasmid pMP90RK was transformed with pAG4015 by electroporation. The plants were transformed following the in planta transformation method described by Clough and Bent, Plant Journal 16:735–743, 1998. Briefly, the Agrobacterium culture containing pAG4015 was grown to an $OD_{600}$ of 1.5 to 2.5. The cells were harvested by centrifugation and resuspended to an $OD_{600}$ of approximately 0.80 in submersion media containing 5% sucrose, 0.04% Silwet L-77, 10 mM MgCl and 44 nM 6-Benzylaminopurine. The plants were inverted into the cell suspension for 15 minutes, then the plants were then placed on their sides under a dome for 16–24 hours to maintain high humidity. The plants were grown for 5 weeks until the siliques were brown and dry. T1 seed was harvested from the plants, surface sterilized and germinated on plates containing ½ MS medium, 0.7% Agar and 50 µg/ml kanamycin monosulfate. Transformed seedlings were identified as those resistant to the kanamycin monosulate. Histochemical staining for GUS activity was performed on the transformants at different stages of development. Seedlings were assayed upon the formation of the first two true leaves (10 days). Plants were also stained after the formation of the rosette (6 to 8 leaves) and upon flowering (approximately 4 weeks). For staining, plants were placed in 1 ml of X-gluc (10 mM EDTA, disodium salt; 100 mM $NaH_2PO4.3H_2O$; 0.5 mM $K4Fe(CN6).3H_2O$; 0.1% Triton X-100; 0.05% x-gluc; 1% DMSO) and incubated at 37 C. for 18–24 hours. After the incubation, the plants were rinsed 3 times with 95% EtOH until the residual stain and plant pigments were cleared, and then the stained tissue was photographed.

The results of staining for GUS reporter gene activity in Arabidopsis stably transformed with the construct pAG4015, presented in FIGS. 11A–D indicate that the mACTIN promoter directs strong reporter gene expression in seedlings as determined by histochemical staining, with GUS staining especially apparent in roots (FIG. 11B). After the formation of the rosette, more intense blue staining was apparent in the cotyledons, early true leaves and roots than in the later developing leaves (FIG. 11C). In mature leaves, the mACTIN promoter is also active, with strong histochemical staining in leaves as well as flowers (FIG. 11D).

EXAMPLE 4

Construction of Modified Melon Actin/TRX Fusion Promoters

Two modified form of the banana fruit-specific TRX promoter were constructed by (1) adding a monocot intron to the 3' end of the banana TRX promoter and (2) by fusing the banana TRX promoter with the melon actin promoter at the TATA-box.

TRX Promoter with Added Monocot Intron

The first modification to the TRX promoter involved the addition of a DNA fragment containing intron 3 from the maize O2 gene to the NcoI site engineered into the 3' end of the banana fruit-specific TRX promoter. The complete nucleotide sequence of the maize O2 gene was obtained from GenBank Accession X15544, within which intron 3 is between nucleotides 3020 to 3105. The maize O2 intron 3 is a typical monocot intron: it is short, only 83 nt; A+U-rich (60%); and contains appropriate consensus splice sites. Oligonucleotides were designed to amplify the maize O2 intron 3 and then subclone it into the NcoI site at the 3' end of the TRX promoter. The oligonucleotide primers used to amplify the maize O2 intron are listed below. The amplification product containing the O2 intron was cloned into an intermediate vector, sequenced to confirm its identity, then subcloned in the correct orientation into the NcoI site engineered into the 3' end of the TRX promoter. After the addition of the intron, there are two potential ATG start codons associated with any linked gene, one at each end of the intron. The construct was designed such that if the added O2 intron is properly spliced, the upstream ATG in the resulting transcript is in-frame with the downstream ATG. In such cases, if translation is initiated from the upstream ATG, the resulting fusion protein will contain four additional amino acids (MEKA) at the N-terminus. If the intron is not properly spliced, the upstream ATG will not be in-frame with the linked gene, but translation can still be initiated from the downstream ATG. In this case, the resulting protein will not contain any additional amino acids. The O2 intron-modified TRX promoter fused to the GUS reporter gene was designated pAG759. The complete nucleotide sequence of the TRX-O2 intron fusion promoter appears in FIGS. 5A–B (SEQ ID NO:5).

The O2int_F (SEQ ID NO:37) and O2int_R (SEQ ID NO:38) oligonucleotides used to amplify intron 3 of the maize O2 gene for subcloning into the NcoI site at the 3' end of the banana TRX promoter are presented below with the NcoI site engineered into the sequence for subcloning indicated as underlined in Table 5.

In a separate modification to the TRX fruit-specific promoter, the banana TRX promoter was fused to the melon actin promoter at the TATA-box, resulting in a fusion promoter having the sequence presented as SEQ ID NO:6. Both promoters contained an identical, canonical plant TATA-box (TATAAA), which was used to perform a perfect fusion between them at that site. Chimeric oligonucleotide primers (shown below) were designed that were complementary to both of the promoter sequences. A fragment containing the banana TRX promoter from the 5' end to the TATA box was amplified from pAG159 using 1233 (SEQ ID NO:42) and (Act)TRX_R (SEQ ID NO:40). The product was approximately 0.8 kb. The melon actin fragment for fusion to the Thi promoter fragment was amplified from pAG167 using GUS5'R (SEQ ID NO:41) and (TRX)Act_F (SEQ ID NO:39) and a PE480 thermal cycler: 25 cycles (94° C., 30 seconds; 60° C., 30 seconds; 72° C., 90 seconds), 1 cycle (72 ° C., 10 min). The 1.2 kb fragment from the melon actin promoter contained the transcription start site, 5' untranslated region intron, and the translational start site that had been engineered to contain an NcoI site for ease of subcloning linked genes. The fragments contained a complementary overlapping region of 21nucleotides, including the TATA-box. The two fragments were fused by combining them in a second amplification reaction and using the end primers (1233 and GUS5'R) for amplification and a PE480 thermal cycler: 25 cycles (94° C., 30 seconds; 60° C., 30 seconds; 72° C., 150 seconds), 1 cycle (72° C. for 10 min). The resulting reaction products were separated on an agarose gel, and the fragment of the correct predicted size was gel purified, digested with HinDIII and NcoI, ligated into a vector containing the GUS reporter gene and given the designation pAG749.

Oligonucleotide primers used to amplify and assemble the TRX-melon actin fusion promoter included (TRX)Act_F (SEQ ID NO:39), (Act)TRX_R (SEQ ID NO:40), GUS5'R (SEQ ID NO:41) and 1233 (SEQ ID NO:42).

Plant Transformation Vectors and Melon Actin/TRX Fusion Promoter Activity Using Reporter Constructs The modified TRX promoters were cloned into expression constructs (as a translational fusion) with the reporter gene encoding GUS, resulting in constructs designated pAG749 (TRX-actin::GUS) and pAG759 (TRX-intron::GUS). The modified TRX promoters were tested for GUS expression in the banana fruit slice transient expression assay described above.

Figure 12A:
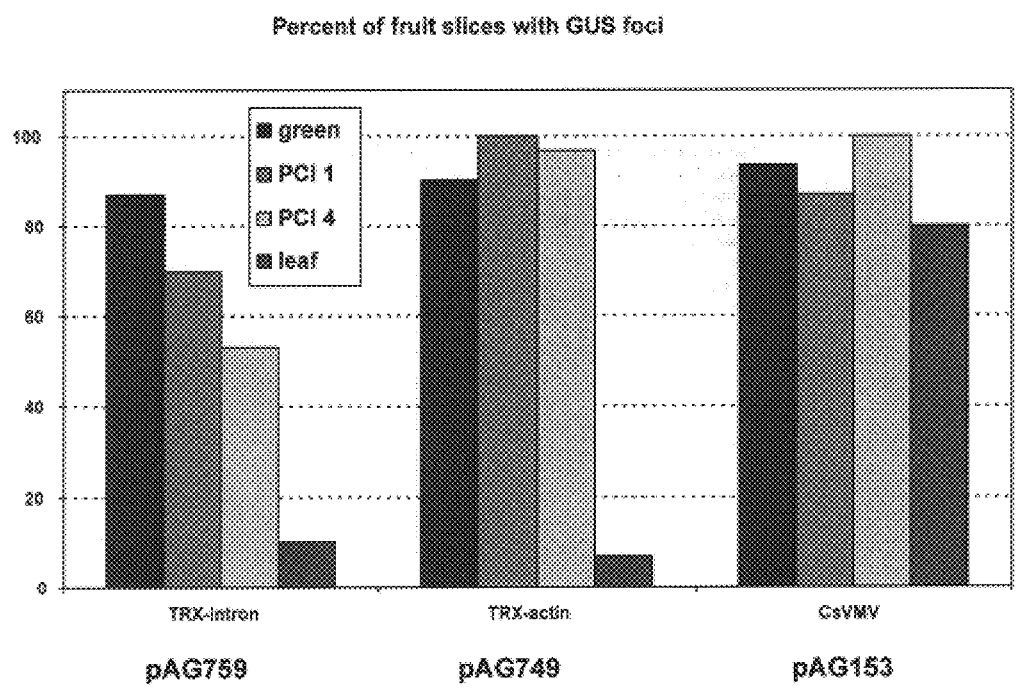
FIGS. 12A and 12B illustrate the relative promoter activity of GUS reporter constructs in banana fruit slices. The TRX-intron (pAG759), and TRX-actin (pAG749), fruit-associated fusion promoters in translational fusion with the reporter gene GUS were introduced into banana fruit slices by microprojectile bombardment. The samples used were either green, non-ethylene-treated fruit (green), green fruit but within 24 h of ethylene treatment (PCI 1), yellow fruit with green tips (PCI 4) or leaf. Relative promoter activity is expressed as both the percent of fruit slices showing foci after histochemical staining (FIG. 11A) and the mean number of foci per fruit slice (FIG. 11B), for the 30 samples tested per group. The strong constitutive CsVMV promoter was used as a positive control for comparison (pAG153).
Figure 12B:
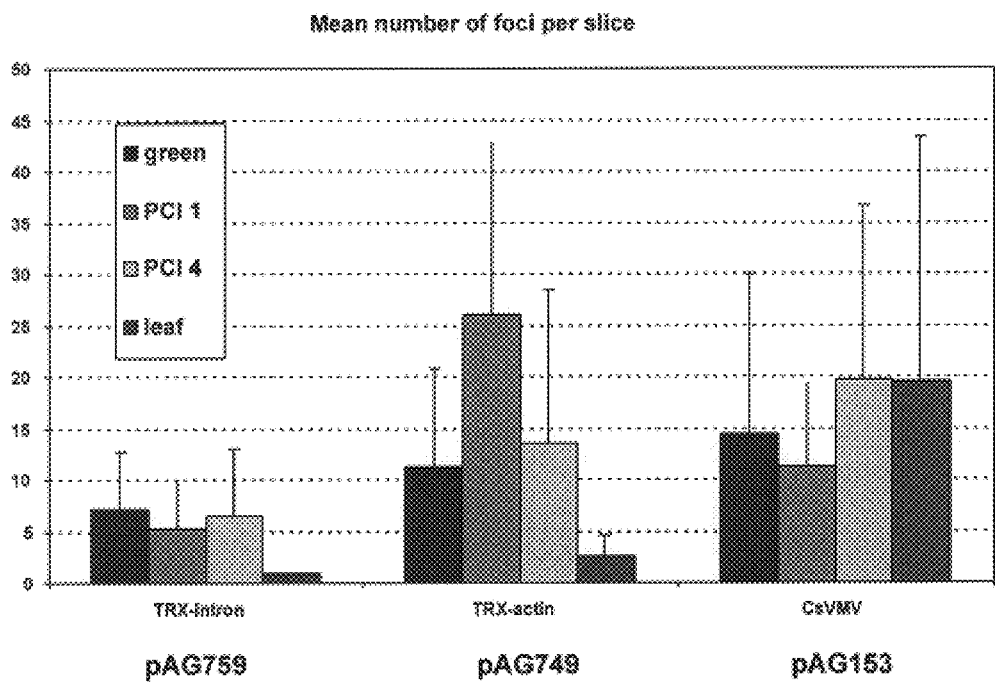

The samples used were either green, non-ethylene-treated fruit (green), green fruit but within 24 h of ethylene treatment (PCI 1), yellow fruit with green tips (PCI 4) or leaf. The relative activity of the TRX-intron, TRX-actin fruit-associated fusion promoters and the CsVMV viral promoter in promoting GUS expression is expressed as both percent of fruit slices showing foci after histochemical staining (FIG. 12A) and mean number of foci per fruit slice (FIG. 12B). in banana fruit slices. The strong constitutive CsVMV promoter was used as a positive control.

According to the transient expression results for the modified TRX promoters, the TRX-intron and TRX-actin modifications have improved performance relative to the banana fruit-specific TRX promoter.

In particular, the TRX-actin fusion promoter displays transient expression activity approximately equal to the strong constitutive promoter CsVMV, whereas the TRX-intron fusion is slightly less active on average. Furthermore, the TRX-intron and TRX-actin promoters have lower activity in banana leaves, indicating that the promoters have retained the tissue specificity of the TRX promoter.

TABLE 4

Banana And Melon Actin Promoter-Containing Nucleic Acid Constructs.

| CONSTRUCT | PROMOTER | LINKED TRANSGENE |
|---|---|---|
| pAG159 | TRX | GUS |
| pAG153 | CsVMV | GUS |
| pBI221 | CaMV35S | GUS |
| pAG142 | PEL2.5 | GUS |
| pAG142a | PEL2.0 | GUS |
| pAG142b | PEL1.4 | GUS |
| pAG142c | PEL0.9 | GUS |
| pAG138M | RE4 | GUS |
| pAG147 | No promoter | GUS |
| pAG167 | mACTIN | GUS |
| pAG4015 | mACTIN | GUS |
| pAG749 | TRX-actin | GUS |
| pAG759 | TRX-O2intron | GUS |

TABLE 5

Sequences Provided In Support Of The Invention.

| Description | SEQ ID NO |
|---|---|
| FIGS. 1A–D: the complete annotated nucleotide sequence of the fruit-associated banana TRX gene (about 2.5 kb) TRX = "G1A")-In the figure, there is only the complete sequence of the G1A gene, including the coding sequence and intron. | 1 |
| FIG. 2: The modified TRX promoter sequence, which corresponds to nucleotides 13–990 of the sequence presented in FIG. 1, with the exception that restriction sites for BamHI and NcoI have been engineered into the sequence in FIG. 2, at the extreme 5' and 3' ends, respectively. | 2 |
| FIG. 3 A–B. Complete sequence of the PEL1 2.0 kb promoter. | 3 |
| FIG. 4: the complete nucleotide sequence of the melon actin promoter as it exists in constructs pAG167 and pAG4015 ("mACTIN"). | 4 |
| FIG. 5 A–B: the complete nucleotide sequence of the banana fruit specific promoter containing intron 3 from the maize O2 gene engineered into the 3' end of the banana fruit-specific TRX promoter ("TRX-INTRON") | 5 |
| FIG. 6: the complete nucleotide sequence of the banana fruit specific promoter TRX fused to the melon actin promoter downstream of the TATA-box ("TRX-ACTIN"). | 6 |
| H-AP1 (5')-AAGCTTGATTGCC-(3') | 7 |
| H-AP2 (5')-AAGCTTCGACTGT-(3') | 8 |
| H-AP3 (5')-AAGCTTTGGTCAG-(3') | 9 |
| H-AP4 (5')-AAGCTTCTCAACG-(3') | 10 |
| H-AP5 (5')-AAGCTTAGTAGGC-(3') | 11 |
| H-AP6 (5')-AAGCTTGCACCAT-(3') | 12 |
| H-AP7 (5')-AAGCTTAACGAGG-(3') | 13 |
| H-AP8 (5')-AAGCTTTTACCGC-(3') | 14 |
| Differential display primer H-T$_{11}$G (5')-AAGCTTTTTTTTTTTG-(3') | 15 |
| Differential display primer H-T$_{11}$A (5')-AAGCTTTTTTTTTTTA-(3') | 16 |
| Differential display primer H-T$_{11}$C (5')-AAGCTTTTTTTTTTTC-(3') | 17 |
| thrdx3'R: (5') GTT GGC AGT GTC TCG ATC GCA CAG TCC (3') | 18 |
| TRX 3'R-2: (5') ATC TCT TGG AAT CAT CAG CTT CAC CAC C (3') | 19 |
| TRX 3'R-3: (5') GAC TTA GTT TGA CAG AAC TTG ATA TGC (3') | 20 |
| TRX 3'UTR: (5') ATC TCC GAG TTC ACG ACC CAA CAC CGA C (3') | 21 |
| TRX 5'F: (5') ATG GCG GAG AAA GGA TCG GTG ATC GG (3') | 22 |
| TRX14 A: (5') GCC ACT AGG AAT CAT GAA ACC TTT GTC GG (3') | 23 |
| TRX14 B: (5') AAG ACG ATG AAC CAA AGC GAC GCG TTG G (3') | 24 |
| TRXP-F: (5') GCT ATT AAG GCT GGA TCC CAA GAC C (3') | 25 |
| TRXP-R: (5') TTT CTC CGC CAT GGC GCT CGA TTC C (3') | 26 |
| PEL 3'R-2: (5')-CCC AGT GGG TGT AGT CAT TGT TCA CC-(3') | 27 |
| PFBAN3'R: (5')-TCT TCC CGA ACC CGA TGG CGC AGT CA-(3') | 28 |

TABLE 5-continued

Sequences Provided In Support Of The Invention.

| Description | SEQ ID NO |
|---|---|
| PF Pec 3'R: (5')-GAG AAG AGT AGA CGG GGG CAG TGA AGG C-(3') | 29 |
| ACTIN 5'F: 5'-ATG ACT CAA ATC ATG TTT GAG ACC TTC -3' | 30 |
| ACTIN 3'R: 5'-ACC TTA ATC TTC ATG CTG CTT GGA GC -3' | 31 |
| PF1: 5'-GTAATACGACTCACTATAGGGC-3' | 32 |
| PF2: 5'-ACTATAGGGCACGCGTGGT-3' | 33 |
| Actin PFb: (5') ATA GGC ATC CTT TTG GCC CAT CCC AAC C (3') | 34 |
| Actin PFc: (5') AGA ATT ACA TCA TTG TCA TTC AAA TGG (3') | 35 |
| MACTP int1 (5') CCT CGC CAT GGG CCC TTT TTT (3') | 36 |
| O2int F 5' AA<u>CCATGG</u>AAAAGGTAACCGCTTGATCG 3' | 37 |
| O2int R 5' AA<u>CCATGG</u>CCTAATTAAAATCAAGTGACAG 3' | 38 |
| (TRX)Act F: 5' GCGCTCCTCTATAAACCCCGTTTC 3' | 39 |
| (Act)TRX R: 5' CGGGGGTTTATAGAGGAGCGCTTCG 3' | 40 |
| GUS5'R: 5' GACTTCGCGCTGATACC 3' | 41 |
| 1233: 5' AGCGGATAACAATTTCACACAGGA 3' | 42 |

It is claimed:

1. An isolated nucleic acid molecule comprising a promoter, wherein the promoter comprises the nucleic acid sequence presented as SEQ ID NO:4.

2. An isolated nucleic acid molecule comprising a promoter, wherein the promoter consists of a portion of the nucleic acid sequence presented as SEQ ID NO:4 that, when operably linked to a protein-encoding polynucleotide sequence, directs expression of the protein in a plant cell.

3. A plant expression vector comprising the nucleic acid molecule of claim 1 or claim 2, wherein the promoter is operably linked to a protein-encoding polynucleotide sequence.

4. The plant expression vector of claim 3, wherein the protein encoding polynucleotide sequence is heterologous with respect to the promoter.

5. The plant expression vector of claim 3, wherein the protein encoding polynucleotide sequence is operably liked to control sequences recognized by a host cell transformed with the vector.

6. A plant cell comprising the plant expression vector of claim 3 in its genome.

7. A method for producing a transgenic plant that exhibits constitutive expression of a protein encoding polynucleotide sequence, comprising:
   (a) transforming plant cells with the plant expression vector of claim 3, and
   (b) growing said transformed plant cells to produce a transgenic plant that exhibits constitutive expression of the structural gene.

8. The plant expression vector of claim 3 wherein the protein encoding polynucleotide sequence encodes a selectable marker.

9. The plant cell of claim 6 wherein the plant cell is dicotyledonous.

10. The plant cell of claim 6 wherein the plant cell is monocotyledonous.

11. The method of claim 7 wherein the protein encoding polynucleotide sequence encodes a selectable marker.

12. The method of claim 7 wherein the plant cells are dicotyledonous.

13. The method of claim 7 wherein the plant cells are monocotyledonous.

* * * * *

UNITED STATES PATENT AND TRADEMARK OFFICE
CERTIFICATE OF CORRECTION

PATENT NO. : 6,642,438 B1  Page 1 of 1
APPLICATION NO. : 09/527972
DATED : November 4, 2003
INVENTOR(S) : Clendennen et al.

It is certified that error appears in the above-identified patent and that said Letters Patent is hereby corrected as shown below:

Drawings,
Figure 4, line 14, should read as follows:
-- CTTCATTCAT TCTCCTCTCT TTCATCCAAG gtttgtttctt ccttcccttt +145 --.
Lines 15-31, change numbers at the right margin to read as follows:
-- 195, 245, 295, 345, 395, 445, 495, 545, 594, 645, 695, 745, 795, 845, 895, 945 and 986 --.

Columns 39-40,
Line 5, "<211>" change "1541" to -- 1542 --.
SEQ ID NO:4, line 12, should read as follows:
tctcctctct ttcatccaag gtttgtttctt ccttcccttt tttaccaaat cttctcactt 721 --.
Lines 13-26, change numbers at the right margin to read as follows:
-- 781, 841, 901, 961, 1021, 1081, 1141, 1201, 1261, 1321, 1381, 1441, 1501 and 1542 --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO.         : 6,642,438 B1
APPLICATION NO. : 09/527972
DATED              : November 4, 2003
INVENTOR(S)     : Clendennen et al.

It is certified that error appears in the above-identified patent and that said Letters Patent is hereby corrected as shown below:

<u>On the Title Page Item (56)</u>
Line 2, "repening" should be --ripening--.

In column 1, line 63, "1989)." should be --(1989).--.
In column 4, line 7, ""TRX-actin," should be --"TRX-actin",--.
In column 7, line 43, "1998)." should be --1998)).--.
In column 8, line 22, "evaluating the of a" should be --evaluating a--.
In column 10, lines 28, "walking an assembled" should be --walking and assembled--.
In column 15, line 53, "ripening;" should be --ripening,--.
In column 16, line 3, "softening);" should be --softening));--.
In column 16, line 26, "promoters" should be --promoters.--.
In column 16, line 34, "comprising;" should be --comprising--.
In column 18, line 3, "fruit" should be --fruit.--.
In column 18, line 7, "[Thomas" should be --(Thomas--.
In column 19, line 13, "PO4.H$_2$O" should be --PO4·H$_2$O--.
In column 19, line 14, "(CN)$_6$.3H$_2$O" should be --(CN)$_6$·3H$_2$O--.
In column 24, line 51, "effective amplify" should be --effective to amplify--.
In column 27, line 39, "bombard" should be --bombarded--.
In column 27, line 48, "bombard" should be --bombarded--.
In column 28, line 56, "(MACTIN)" should be --(mACTIN)--.
In column 29, line 2, "contains" should be --which contains--.
In column 29, line 36, "PO4.H$_2$O" should be --PO4·H$_2$O--.
In column 29, line 37, "(CN)$_6$.3H$_2$O" should be --(CN)$_6$·3H$_2$O--.
In column 29, line 56, "form" should be --forms--.

*Claim 7, at col. 55, lines 10-17, reads:*

> 7. A method for producing a transgenic plant that exhibits constitutive expression of a protein encoding polynucleotide sequence, comprising:
> (a) transforming plant cells with the plant expression vector of claim 3, and
> (b) growing said transformed plant cells to produce a transgenic plant that exhibits constitutive expression of the structural gene.

UNITED STATES PATENT AND TRADEMARK OFFICE
CERTIFICATE OF CORRECTION

PATENT NO. : 6,642,438 B1
APPLICATION NO. : 09/527972
DATED : November 4, 2003
INVENTOR(S) : Clendennen et al.

It is certified that error appears in the above-identified patent and that said Letters Patent is hereby corrected as shown below:

*and correctly should read:*

> 7. A method for producing a transgenic plant that exhibits constitutive expression of a protein encoding polynucleotide sequence, comprising:
> (a) transforming plant cells with the plant expression vector of claim 3, and
> (b) growing said transformed plant cells to produce a transgenic plant that exhibits constitutive expression of the protein encoding polynucleotide sequence.

Signed and Sealed this

Fifth Day of August, 2008

JON W. DUDAS
*Director of the United States Patent and Trademark Office*

SEQUENCE LISTING

<160> NUMBER OF SEQ ID NOS: 42

<210> SEQ ID NO 1
<211> LENGTH: 2453
<212> TYPE: DNA
<213> ORGANISM: Banana
<220> FEATURE:
<221> NAME/KEY: misc_feature
<222> LOCATION: (1)...(2453)
<223> OTHER INFORMATION: n = A,T,C or G

<400> SEQUENCE: 1

```
gctattaagg cttgatccca agaccctcgc tctctatctt cgcaacaact cacgtcattg      60
ttattggttc ccttttgcc ttcgtctcaa atgtctcata ttgtataatc ttcaagaagg     120
gtattcacga cctcctacga tgaaggagtg caccctcgtc tgctttcgtt tcttatcatt     180
gcttcgttag ggaaacataa taactcggga aggagacaca aacaatgttt atagtgatga     240
gtcatgtaag gaaggagaga agaaagttgt gtcgtgattg cctccttccc cttaacctt     300 gttggatgaa aaagatcatt aggactcgaa attttaaaag gtggagaagg agacccaaga     360
taccctcctc atagcaagat aagagatatc cgagatgaat gtgaggaaga aaacgatagc     420
aaacgatgta agttatcatg aaaataaaga gaaaatatga gaacctcatg atgaggcttt     480
agtgtcacct cgataattaa agacgaggat aacaacgtga caacaataac caacaaggga     540
cataaacgat aaaggcgttg attgacgaga ccaaagtcga acataataat attttttaa     600 gataaaaaaa aaagtaaaag gatgtatttt agaagaaaag aaataaaaga ttataatttt     660
tttgagaatt tgtccgaata cgaatatata ttattttgaa tattaattaa ataaagatac     720
caacgcgtcg ctttggttca tcgtctttct ttaacgcggc ggacgggaac gtgaggccga     780
caaaggtttc atgattccta gtggcgtctt tatgatttcc actctgatgc tgatggaaac     840
gtgagcggcg aaagaagcgc cacaattgat cgaagcgctc ctctataaat ggcgagtacc     900
gggagggagc ctcaagcagt gccttgtccc ggttgattcg agtcccgtcc tccgatttcg     960
tgcaagaaga gaagggaatc gagcgagatg gcggagaaag gatcggtgat cgggtgccac    1020
accatcgccc agtggaaccg gcagctccaa ctcgccagcg agtccgggaa gctggtaagg    1080
ttccgacttg ctcgacccct tgtgtttgct tctanggttt tgggggtaaa tgtccattgc    1140
```

-continued

```
gacctcgtca tggaaacacc aactcttttc ttgcactaaa aacccngcat tggcagagga    1200
gctttatatg ccgagcttag aattttagac tcagggtttt gagtcattct ttataggatt    1260
ttatgagttg atattatttt ctatgctcta tctgttgatt tatattggtc taagatcatt    1320
gttattgtgc aagaatttta cagagggaaa ggtaatgaca gaaaaagaaa ggagagtgcc    1380
atcaaatgct atttgggtgc caagggacaa atttgttctg atgccatgtt ccattctttg    1440
accctaatgt ctaatatcaa tggtatctga attaaacgat gtcattgtga cggtggatgt    1500
ctaatgtcta agttacagaa aacaaaggag ggtgtcatca aatgctatta tctggtaatt    1560
ggatgccaag gggcaaatta tcatggtgtc taatcaatga tatctaattt aaaggctact    1620
gcctaaagcc caacctttc ttcctttatt tattttaatt gttaactctt tatttgaact    1680
tttatattct gtgtgtactc cacttaattg agcatatcaa gttctgtcaa actaagtcta    1740
tcaaactttt ggtggtgaag ctgatgattc aagagatca ggaagatctt tctattcaac    1800
atccatgttt tttcttatac cattgtttac aacttagtta catctttct tccgttcctg    1860 tttcataaat gcatatttat tttctgaaaa atgtaaagct aaacagagtc gaaatctatc    1920
aaactgctgc atctcttgtt ggctctaaag atttgtctgg tttacaggtg gtcgtagatt    1980
tcacttcttc atggtgtggt ccttgccgta tgattgcccc gttcttcgct gagctagcta    2040
ataagttcac cgatgccatc ttcctaaggg tggacgtcaa tgagctgaag gtaaaaacta    2100
tcaacatgca gattaaactc gtgccgctgt tgtttgcgag gtgaaattat gtttctaatt    2160
ctccaacctg tgtcaccaaa cggcagaggg ttgccctgga ctgtgcgatc gagacactgc    2220
caaccttcat cttcctgagg caggaaaaca ttgtggatcg cgttgttggt gctcgtaaag    2280
atctgttgcc gaagaagatt gagctccaca tgaggaactg aatgctcgct tgcagtatta    2340
gtgtcggtgt tgggtcgtga actcggagat tttgtggggt tagaataaac atatgtactg    2400
aattccatcg gttcatgatt atattaacta ttgaataaac tagtctttca tcc            2453
```

<210> SEQ ID NO 2
<211> LENGTH: 979
<212> TYPE: DNA
<213> ORGANISM: Artificial Sequence
<220> FEATURE:
<223> OTHER INFORMATION: TRX promoter

<400> SEQUENCE: 2

```
ggatcccaag accctcgctc tctatcttcg caacaactca cgtcattgtt attggttccc      60
tttttgcctt cgtctcaaat gtctcatatt gtataatctt caagaagggt attcacgacc     120
tcctacgatg aaggagtgca ccctcgtctg ctttcgtttc ttatcattgc ttcgttaggg     180
aaacataata actcgggaag gagacacaaa caatgtttat agtgatgagt catgtaagga     240
aggagagaag aaagttgtgt cgtgattgcc tccttcccct taacctttgt tggatgaaaa     300
agatcattag gactcgaaat tttaaaaggt ggagaaggag acccaagata ccctcctcat     360
agcaagataa gagatatccg agatgaatgt gaggaagaaa acgatagcaa acgatgtaag     420
ttatcatgaa aataaagaga aaatatgaga acctcatgat gaggctttag tgtcacctcg     480
ataattaaag acgaggataa caacgtgaca acaataacca acaagggaca taaacgataa     540
aggcgttgat tgacgagacc aaagtcgaac ataataatat ttttttaaga taaaaaaaa     600 agtaaaagga tgtatttag aagaaagaa ataaagatt ataatttttt tgagaatttg      660
tccgaatacg aatatatatt attttgaata ttaattaaat aaagataccca acgcgtcgct     720 ttggttcatc gtctttcttt aacgcggcgg acgggaacgt gaggccgaca aaggtttcat     780
```

-continued

```
gattcctagt ggcgtcttta tgatttccac tctgatgctg atggaaacgt gagcggcgaa      840
agaagcgcca caattgatcg aagcgctcct ctataaatgg cgagtaccgg gagggagcct      900
caagcagtgc cttgtcccgg ttgattcgag tcccgtcctc cgatttcgtg caagaagaga      960
agggaatcga gcgccatgg                                                   979
```

<210> SEQ ID NO 3
<211> LENGTH: 2010
<212> TYPE: DNA
<213> ORGANISM: Artificial Sequence
<220> FEATURE:
<223> OTHER INFORMATION: PEL1 2.0kb promoter

<400> SEQUENCE: 3

```
aaagaaagat gtgcaggtgt taaccttggt gtttgatgga acacaagact ctttatcaac       60
aatatgatga cattagaaca agcagctgac acgcattact tttgatcaag ataggctgct      120
cttgatcctc tcagcagcag acagaatgta cttattcttg ctatttgtct caatcatgca      180
gaatgatgtg gctaaatcaa tactttcatt gaacaactag aacatgattt ctcataaatt      240
tatcggaaga tatataatta gactcaaaac cagcagaaca ctacaccagt tgttagttgc      300
agcaaaaaat aatattgtca acaagaagct agcagctatt tacttcttca gcttctcctc      360
aagcttcaag taaaggattt gggattgttc ctaagaaggc agggctactt aatgcgacat      420
taccacatga tatgcatatc tacctctgaa aactgtttcc atggctttca atcacattgt      480
actataaatc taagggaaga aaagtgcacg ctttgacttt gaattcattt gttgacgctt      540
agtacatcaa tggtgtgatc tgctgcatac tgcaagttgg atgcaacttg taagagctag      600
aacacgatgg tagactgtca agctctttga atgggttttg ccctgtgacc atggaaagct      660
agagcgagag agagggagag agagatgacg gttggagagg agccatcaca ctatccaaca      720
caattagagg gtgggcataa aaaaggccat gtgggccgcg aaaagagacc tctccttccc      780
tcccccatcg cgtcgcggac ggacgggatc gtcctaatgt cgtgatcgac ggcccacata      840
ctcacccgag atcgaccgac ggggcccacg ccgcgagggg aatggtggga agctcacgtg      900
ggagaaacat gcgctgccgg ccacctcatc ttcatcatca acagaaacga gtggaagccc      960
acccgctgac atggcacaat cgcagcgggc tcgatcgata caagtcaggc cgcgctctgc     1020
ggccgaaagc catcccatgt gctgtgcagt gccgtgaaca cccctattgt atccctttct     1080
tccttcgcat gtgtagtcac agtaacaaga tcatgactcc gaatccatgg agctcctgca     1140
tcttggacga gtttggtgta cccaaagagg acgcattgat gagcgtgccg agatcccagg     1200
tattggtcat ggcaattacc cccattcacc tttgctagca gagtaataac cgtgaatcgg     1260
atgttaagtt gcttagagac tcttgggact tcatcaatgc tacgggacca gattgagcca     1320
cagcaccaac ctgcgcttct ctctggaaca aggcagtggt tggaatgcgc aaacgccagc     1380
agttcaatct ttcgctgcac tgtctgcgtc cacaatccat tctggggttt ttcaactctg     1440
cctgacactc gccatgtgag ggctaaagtt gagacaccag caacaataac tgttctccgt     1500
tcctcgataa cttagggttc tcattcatta atgttctggg caattcaatt ggcctccatg     1560
ccctctttca gccctgagac agagtcttct ctgatgttgt actaccaaag cttactgtag     1620
tatcatgtct ctggttgtta agaagacaat agaacagaca tggcaatggg aggtaatgta     1680
tatatgcatc tgaataatta ttctctcagt gttttgttct tgagggcatg gtggcttggt     1740
agtcaaatct accaaaagat gaacggagag gaacagagta tgtgtggaga aaggtgcgtc     1800
```

```
acgttcccca ttatctttag cttctaagat tccccaaatc acgtaccttt ttggacccca   1860
ccggcataga ttgttcacac gacttcctct ctcttccttc tctcatccat agcatcctct   1920
gcctttaaat cccttcgttc ctcttcgcat tactcacaac tctcaactta cgctgccatt   1980
tttgttctta cgggtggtca gtcccttatg                                    2010

<210> SEQ ID NO 4
<211> LENGTH: 1541
<212> TYPE: DNA
<213> ORGANISM: Artificial Sequence
<220> FEATURE:
<223> OTHER INFORMATION: melon actin promoter

<400> SEQUENCE: 4
cccgggctgg tagaatggtt ggaatgaaaa aaattatatt ttctcaccgt tcatattta     60 taaggtggtg aagaaattat tccaattgaa tatttttttt gtaattgtgt ggacataata   120
taaatttatg aatatttatg aattgaagaa aggcaaaggc cacaagaggt gaatgaaagc   180
gatatcataa aaccaaaaaa cacaaattca attttcaaat ttcaaaaaat tgggggctcc   240
aattccaaat tctcagcaag ccgaagccga gcagaagccg aaaataaaga tccaacggtg   300
gagattaaag aaatgaaaaa agaggaaaaa gaaggaaga  agaaaggaag aatgggggctg  360 ggaaaggctg tcagccaggt caccctatct tctctggtgg tcgaaatgat tccttctcca   420
aatttctcat ttccttcgca tttgcatttg catttgcatt tccttctctt ccctctctct   480
ctctctctct ctctctctct ctctctgttt ataaaccccc gtttctcttc ttccctcttc   540
ctcttattct cgtctttcaa ctcacctagg tcgacaacac tcactcctct ctcagccaga   600
ccttcttctt tggagggttg gctctttctt cttcgttcgt tccttccttc cttcattcat   660
tctcctctct ttcatccaag gttgtttctt ccttcccttt tttaccaaat cttctcactt   720
cccttacatt tttcatctgg ggtatcgttc ttttcccaaa ttatgctgct ttcgtctctc   780
atttatctac tttattgctt ttaactcatt ttcccttatg cggttcttca attttggctg   840
atcttgctgt ttgttttgga attctgtttt aatcgccctg gatccgaggt ttttgttcgt   900
acaatctacc tagattcttt ctgtttgttt gctgatctga aattttccat ttgggttttg   960
attgtctgtg cttacggaac tgagatctag gatttggagt tgtgtacctt tttatttctg  1020
catgcaattc tgtaatcctg catagctgga tggctttctg ttgattagtg catgctttgt  1080
ttaggacgaa ctgacttgga ttttcgttg tcgatctgtt ctattttttg ttttgctgtt   1140
ctggttcatg cttggaatga tttagttgct ttgtaaattg tacactctgc ttttgtgtta   1200
gttcacgtag cttctcgatc tgaaattgga tatggttaga gttatggtc  agcttgtgat   1260 cttgcattat gcaaaaattg gaactttaat cctttttcatt tgtaagatct ttaagatatc  1320
tgattacctg gttgattttt ttgtgtctgg attattttat ttgttttgaa agtagtttgt   1380
tggttcttcc tgtattattt gctgaatcgg gatgatcaat tatatgacgt gaatttatgg   1440
aatgtaaatg aatggtttaa gagattgctt tgtgtggctt atttattcaa tttctatttt   1500
tacatcgttt tgtgcaggtt ttgaaaaaaa agggcccatg g                       1541

<210> SEQ ID NO 5
<211> LENGTH: 1074
<212> TYPE: DNA
<213> ORGANISM: Artificial Sequence
<220> FEATURE:
<223> OTHER INFORMATION: promoter

<400> SEQUENCE: 5
```

-continued

```
ggatcccaag accctcgctc tctatcttcg caacaactca cgtcattgtt attggttccc        60
tttttgcctt cgtctcaaat gtctcatatt gtataatctt caagaagggt attcacgacc       120
tcctacgatg aaggagtgca ccctcgtctg ctttcgtttc ttatcattgc ttcgttaggg       180
aaacataata actcgggaag gagacacaaa caatgtttat agtgatgagt catgtaagga       240
aggagagaag aaagttgtgt cgtgattgcc tccttcccct taacctttgt tggatgaaaa       300
agatcattag gactcgaaat tttaaaaggt ggagaaggag acccaagata ccctcctcat       360
agcaagataa gagatatccg agatgaatgt gaggaagaaa acgatagcaa acgatgtaag       420
ttatcatgaa aataaagaga aaatatgaga acctcatgat gaggctttag tgtcacctcg       480
ataattaaag acgaggataa caacgtgaca acaataacca acaagggaca taaacgataa       540
aggcgttgat tgacgagacc aaagtcgaac ataataatat tttttaaga taaaaaaaaa       600 agtaaaagga tgtattttag aagaaaagaa ataaaagatt ataattttttt tgagaatttg       660 tccgaatacg aatatatatt attttgaata ttaattaaat aaagatacca acgcgtcgct       720
ttggttcatc gtctttcttt aacgcggcgg acgggaacgt gaggccgaca aaggtttcat       780
gattcctagt ggcgtcttta tgatttccac tctgatgctg atggaaacgt gagcggcgaa       840
agaagcgcca caattgatcg aagcgctcct ctataaatgg cgagtaccgg gagggagcct       900
caagcagtgc cttgtcccgg ttgattcgag tcccgtcctc cgatttcgtg caagaagaga       960
agggaatcga gcgccatgga aaaggtaacc gcttgatcga tttgcagctt attgtacggg      1020
gttttttaac tcctgggctt atcgatctgt cacttgattt taattaggcc atgg            1074
```

<210> SEQ ID NO 6
<211> LENGTH: 1925
<212> TYPE: DNA
<213> ORGANISM: Artificial Sequence
<220> FEATURE:
<223> OTHER INFORMATION: promoter

<400> SEQUENCE: 6

```
aagcttggta ccgagctcgg atcccaagac cctcgctctt tatcttcgca acaactcacg        60
tcattgttat cggttcccct tttgccttca tctcaaatgt ctcatattgt ataatcttca       120
agaagggtat tcacgacctc ctacgatgaa ggagtgcacc ctcgcctgct ttcgtttctt       180
atcattgctt cgttagggaa acataataac tcgggaagga gacacaaaca atgtttatag       240
tgatgaagtc atgtaaggaa ggagagaaga aagttgtgtc gtgattgcct ccttcccctt       300
aacctttggt ggatgaaaaa gatcattagg actcgaaatt taaaaggtgg agaaggagac       360
ccaagatacc ctcctcatag caagataaga gatatccgag atgaatgtga ggaagaaaac       420
gatagcaaac gatgtaagtt atcatgaaaa taaagagaaa atatgagaac ctcatgatga       480
ggctttagtg tcacctcgat aattaaagac gaggataaca acgtgacaac aataacaaac       540
aagggacata acgataaag gcgttgattg acgagaccaa agtcgaacat aataatattt       600
ttttaagata aaaaaaaag taaaggatg tattttagaa gaaaagaaat agaagattat       660 aattttttg agaatttgtc cgaatacgaa tatatattat tttgaatatt aattaaataa       720
agataccaac gcgtcgcttt ggttcatcgt ctttctttaa cgcggcggac gggaacgtga       780
ggcggacaaa ggtttcatga ttcctagtgg cgtctttatg atttccactc tgatgctgat       840
ggaaacgtga gcggcgaaag aagcgccaca attgatcgaa gcgctcctct ataaaccccc       900
gtttctcttc ttccctcttc ctcttattct cgtctttcaa ctcacctagg tcgacaacac       960
```

-continued

```
tcactcctct ctcagcctag accttcttct ttggagggtt ggctctttct tcttcgttcg    1020
ttccttcctt ccttccttca ttctcctctc tttcatccaa ggtttgtttc ttccttccct    1080
tttttaccaa atcttctcac ttcccttaca tttttcatct ggggtatcgt tcttttccca    1140
aattatgctg ctttcgtctc tcatttatct actttattgc ttttaactca ttttcccttta   1200 tgcggttctt caattttggc tgatcttgct gttttgttttg gaattctgtt ttaatcgccc    1260
tggatccgag gttttagtt cgtacaatct acctagattc tttctagttt gtttgctgat     1320
ctgaaatttt ccatttgggt tttgattgtc tgtgcttacg gaactgagat ctaggatttg    1380
gagttgtgta cctttttatt tctgcatgca attctgtaat cctgcatagc tggatggctt    1440
tctgttgatt agtgcatgct ttgtttagga cgaactgact tggatttttc gttgtcgatc    1500
tgttctattt tttgttttgc tgttctggtt catgcttgga atgatttagt tgctttgtaa    1560
attgtacact ctgcttttgt gttagttcac gtagcttctc gatctgaaat tggatatggt    1620
tagagtttat ggtcagcttg tgatcttgca ttatgcaaaa attggaactt taatccttttt   1680 catttgtaag atctttaaga tatctgatta cctggttgat ttttttgtgt ctggattatt    1740
ttatttgttt tgaaagtagt ttgttggttc ttcctgtatt atttgctgaa tcgggatgat    1800
caattatatg acgtgaattt atggaatgta aatgaatggt ttaagagatt gctttgtgtg    1860
gcttatttat tcaatttcta tttttacatc gttttgtgca ggttttgaaa aaaagggcc    1920 catgg                                                                1925
```

<210> SEQ ID NO 7
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 7
aagcttgatt gcc                                                        13

<210> SEQ ID NO 8
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 8
aagcttcgac tgt                                                        13

<210> SEQ ID NO 9
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 9
aagctttggt cag                                                        13

<210> SEQ ID NO 10
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 10
aagcttctca acg                                                    13

<210> SEQ ID NO 11
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 11
aagcttagta ggc                                                    13

<210> SEQ ID NO 12
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 12
aagcttgcac cat                                                    13

<210> SEQ ID NO 13
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 13
aagcttaacg agg                                                    13

<210> SEQ ID NO 14
<211> LENGTH: 13
<212> TYPE: DNA
<213> ORGANISM: Artificial Sequence
<220> FEATURE:
<223> OTHER INFORMATION: oligonucleotide primer

<400> SEQUENCE: 14
aagcttttac cgc                                                    13

<210> SEQ ID NO 15
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 15 aagcttttttt tttttg                                                16

<210> SEQ ID NO 16
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 16 aagcttttttt tttta                                                 16

<210> SEQ ID NO 17
<211> LENGTH: 16
<212> TYPE: DNA

```
<213> ORGANISM: Artificial Sequence
<220> FEATURE:
<223> OTHER INFORMATION: oligonucleotide primer

<400> SEQUENCE: 17
aagctttttt ttttc                                                    16

<210> SEQ ID NO 18
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 18
gttggcagtg tctcgatcgc acagtcc                                       27

<210> SEQ ID NO 19
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 19
atctcttgga atcatcagct tcaccacc                                      28

<210> SEQ ID NO 20
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 20
gacttagttt gacagaactt gatatgc                                       27

<210> SEQ ID NO 21
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 21
atctccgagt tcacgaccca acaccgac                                      28

<210> SEQ ID NO 22
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 22
atggcggaga aaggatcggt gatcgg                                        26

<210> SEQ ID NO 23
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 23
gccactagga atcatgaaac ctttgtcgg                                     29
```

<210> SEQ ID NO 24
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 24
aagacgatga accaaagcga cgcgttgg                               28

<210> SEQ ID NO 25
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 25
gctattaagg ctggatccca agacc                                  25

<210> SEQ ID NO 26
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 26
tttctccgcc atggcgctcg attcc                                  25

<210> SEQ ID NO 27
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 27
cccagtgggt gtagtcattg ttcacc                                 26

<210> SEQ ID NO 28
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 28
tcttcccgaa cccgatggcg cagtca                                 26

<210> SEQ ID NO 29
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 29
gagaagagta gacgggggca gtgaaggc                               28

<210> SEQ ID NO 30
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 30
atgactcaaa tcatgtttga gaccttc                              27

<210> SEQ ID NO 31
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 31
accttaatct tcatgctgct tggagc                               26

<210> SEQ ID NO 32
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 32
gtaatacgac tcactatagg gc                                   22

<210> SEQ ID NO 33
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 33
actatagggc acgcgtggt                                       19

<210> SEQ ID NO 34
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 34
ataggcatcc ttttggccca tcccaacc                             28

<210> SEQ ID NO 35
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 35
agaattacat cattgtcatt caaatgg                              27

<210> SEQ ID NO 36
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 36
cctcgccatg ggccctttt t                                     21

<210> SEQ ID NO 37
<211> LENGTH: 28

```
<212> TYPE: DNA
<213> ORGANISM: Artificial Sequence
<220> FEATURE:
<223> OTHER INFORMATION: oligonucleotide primer

<400> SEQUENCE: 37
aaccatggaa aagtaaccg cttgatcg                                          28

<210> SEQ ID NO 38
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 38
aaccatggcc taattaaaat caagtgacag                                       30

<210> SEQ ID NO 39
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 39
gcgctcctct ataaaccccc gtttc                                            25

<210> SEQ ID NO 40
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 40
cgggggttta tagaggagcg cttcg                                            25

<210> SEQ ID NO 41
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 41
gacttcgcgc tgatacc                                                     17

<210> SEQ ID NO 42
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 42
agcggataac aatttcacac agga                                             24
```